(12) United States Patent
Noujaim et al.

(10) Patent No.: US 11,014,971 B2
(45) Date of Patent: May 25, 2021

(54) PEPTIBODIES, COMPOSITIONS THEREOF, AND METHODS OF TREATING ATRIAL FIBRILLATION

(71) Applicant: University of South Florida, Tampa, FL (US)

(72) Inventors: Sami Fouad Noujaim, Land O Lakes, FL (US); Michael Teng, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 16/369,822

(22) Filed: Mar. 29, 2019

(65) Prior Publication Data

US 2019/0225658 A1 Jul. 25, 2019

Related U.S. Application Data

(63) Continuation of application No. PCT/US2017/064352, filed on Dec. 1, 2017.

(60) Provisional application No. 62/428,749, filed on Dec. 1, 2016.

(51) Int. Cl.

| | | |
|---|---|---|
| C07K 14/435 | (2006.01) | |
| C07K 16/00 | (2006.01) | |
| A61K 47/65 | (2017.01) | |
| A61K 47/68 | (2017.01) | |
| A61P 9/06 | (2006.01) | |
| C07K 16/28 | (2006.01) | |
| A61K 38/00 | (2006.01) | |

(52) U.S. Cl.
CPC ........ *C07K 14/43572* (2013.01); *A61K 47/65* (2017.08); *A61K 47/68* (2017.08); *A61P 9/06* (2018.01); *C07K 16/00* (2013.01); *C07K 16/28* (2013.01); *A61K 38/00* (2013.01); *C07K 2317/52* (2013.01); *C07K 2319/30* (2013.01); *C07K 2319/55* (2013.01); *C07K 2319/70* (2013.01)

(58) Field of Classification Search
CPC .............. C07K 14/43572; A61K 47/68; A61K 47/6801; A61K 47/6803
See application file for complete search history.

(56) References Cited

U.S. PATENT DOCUMENTS

| | | | | |
|---|---|---|---|---|
| 6,660,843 B1 * | 12/2003 | Feige | ............... | C07K 14/505 530/391.7 |
| 8,907,071 B2 * | 12/2014 | Sullivan | ........... | C07K 14/43504 536/23.4 |
| 2003/0166877 A1 | 9/2003 | Gillies et al. | | |
| 2007/0270352 A1 | 11/2007 | Bartlett et al. | | |
| 2013/0096050 A1 | 4/2013 | Shandler | | |
| 2016/0159863 A1 | 6/2016 | Barbas, III | | |

FOREIGN PATENT DOCUMENTS

| | | |
|---|---|---|
| WO | 00/01401 A1 | 1/2000 |
| WO | 2006116156 A2 | 11/2006 |
| WO | 2015150968 A2 | 10/2015 |

OTHER PUBLICATIONS

Shimamoto et al. "Peptibodies: A flexible alternative format to antibodies", mAbs, 2012, 586-591 (Year: 2012).*
Hashimoto "Acetylcholine-Activated Potassium Channel as a Novel Target for AF Treatment, Atrial Fibrillation—Basic Research and Clinical Applications", 2012, pp. 322-338 (Year: 2012).*
Kitamura et al. "Tertiapin Potently and Selectively Blocks Muscarinic K+ Channels in Rabbit Cardiac Myocytes", The Journal of Pharmacology and Experimental Therapeutics, 2005, pp. 196-205 (Year: 2005).*
Humberto Carrillo and David Lipman, The Multiple Sequence Alignment Problem in Biology, Siam J Applied Math, 1988, 48(5), 1073-1082.
Needleman, A general method applicable to the search for similarities in the amino acid sequence of two proteins. J Mol Biol 1970, 48, 443-453.
Dall'Acqua WF, et al., Properties of human IgG1s engineered for enhanced binding to the neonatal Fc receptor (FcRn) J Biol Chem, 2006, 281:23514-23524.
Podd, et al., Are implantable cardiac monitors the 'gold standard' for atrial fibrillation detection? A prospective randomized trial comparing atrial fibrillation monitoring using implantable cardiac monitors and DDDRP permanent pacemakers in post atrial fibrillation ablation patients. Europace (2016) 18, 1000-1005.

(Continued)

*Primary Examiner* — Lianko G Garyu
(74) *Attorney, Agent, or Firm* — Meunier Carlin & Cutfman LLC

(57) ABSTRACT

Described herein are peptibodies that can contain a TertiapinQ peptide, formulations thereof, and uses thereof. In some embodiments, the peptibody can include a first monomer and a second monomer, wherein each monomer can include an Fc polypeptide, a first TertiapinQ peptide, wherein the N-terminus of the first TertiapinQ peptide can be linked to the C-terminus of the Fc polypeptide via a first linker, and wherein the first monomer and the second monomer can be attached via a disulfide bridge between the Fc polypeptide of the first monomer and the Fc polypeptide of the second monomer. The compositions and formulations thereof can be used to treat atrial fibrillation.

16 Claims, 22 Drawing Sheets

Specification includes a Sequence Listing.

(56) References Cited

OTHER PUBLICATIONS

Walfridsson et al., Is the acetylcholine-regulated inwardly rectifying potassium current a viable antiarrhythmic target? Translational discrepancies of AZD2927 and A7071 in dogs and humans, Europace (2015) 17, 473-482.
International Search Report and Written Opinion issued for Application No. PCT/US2017/064352, dated Mar. 7, 2018.
Supplementary Search Report issued for European Application No. 17875219, dated Mar. 9, 2020.

* cited by examiner

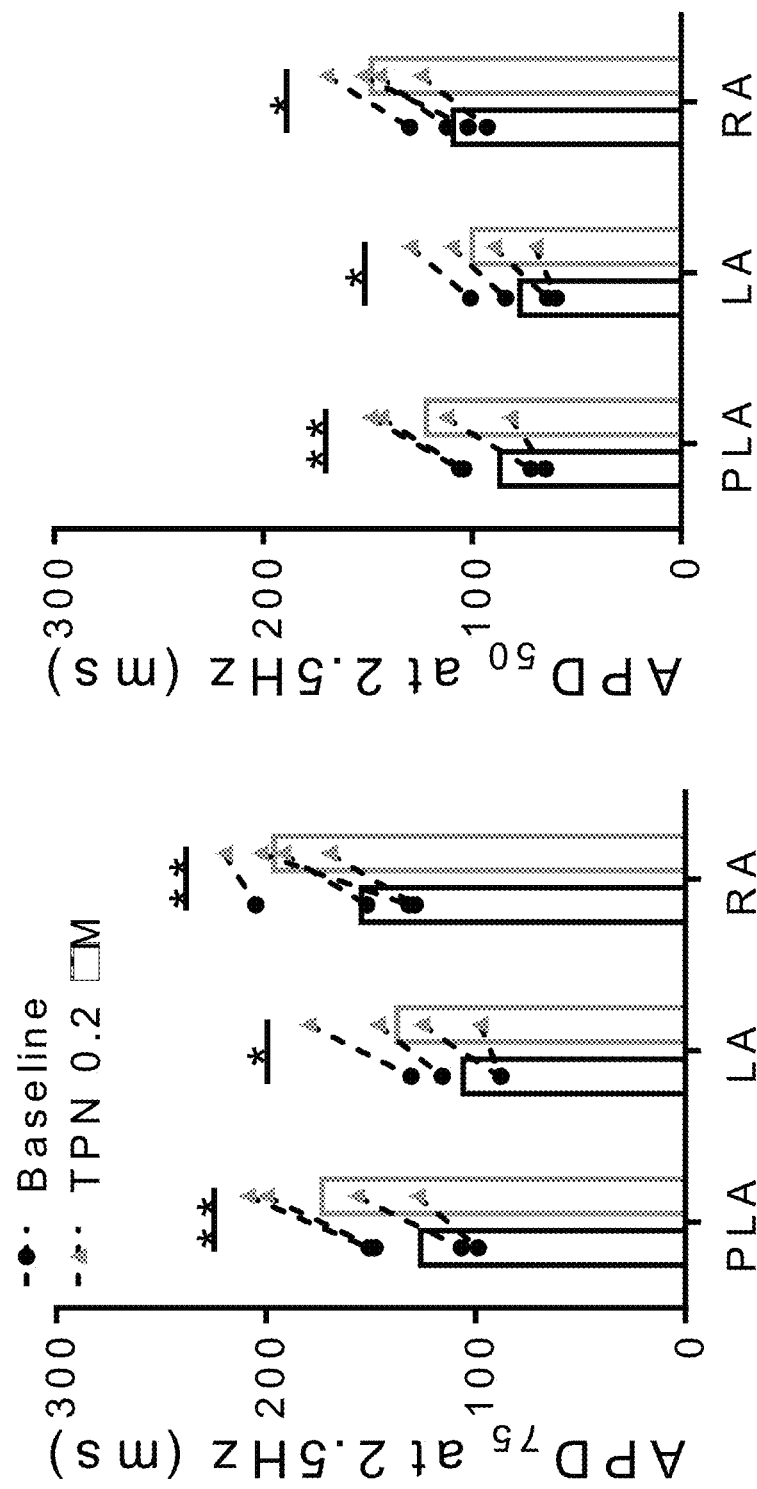

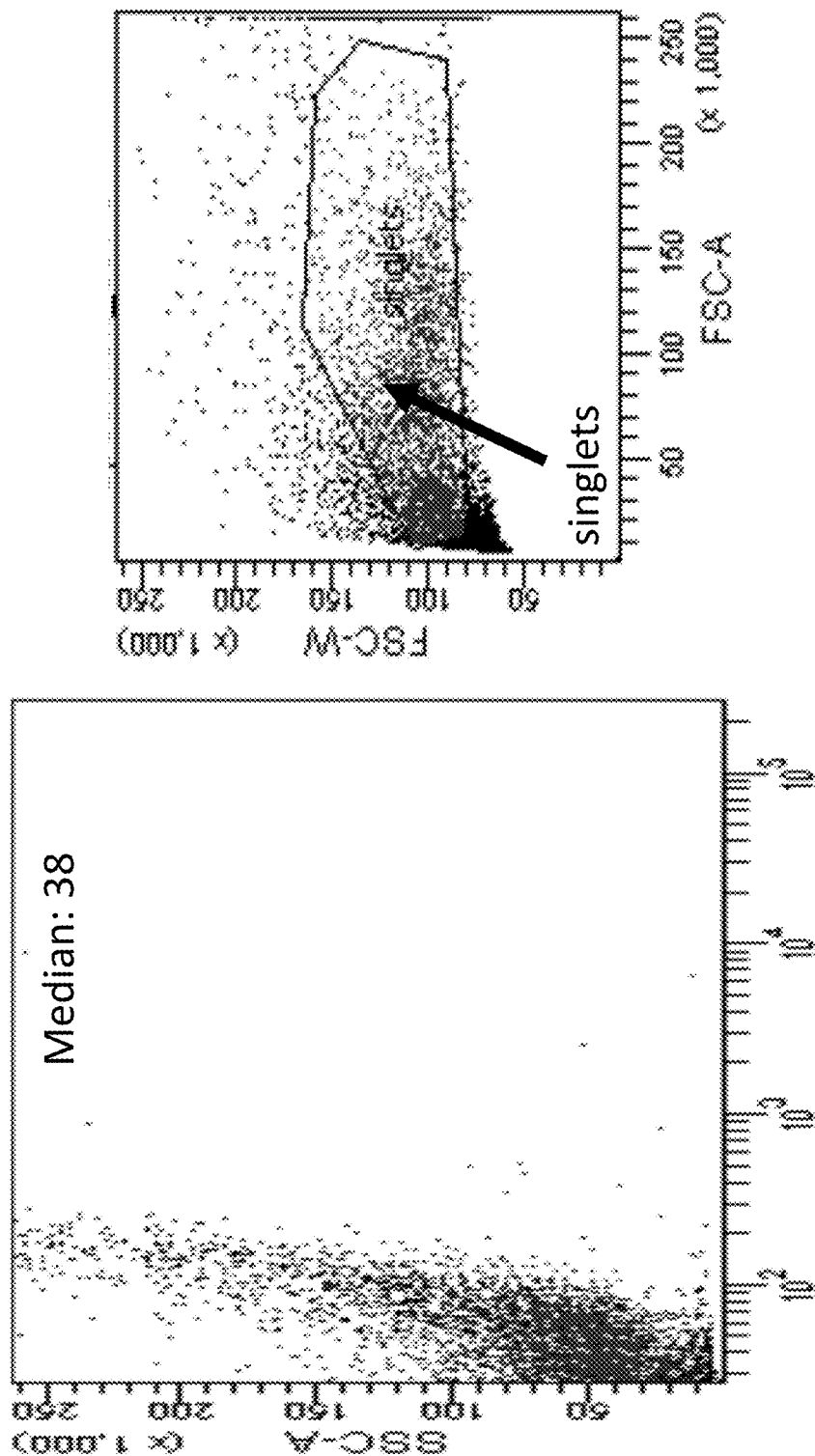

SEQ ID NO: 1

ASTKGPSVFPLAPSSKSTSGGTAALGCLVKDYFPEPVTVSWNSGALTSGVHTFPAVLQSSGLY

SLSSVVTVPSSSLGTQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREEQYNSTYRVVSVLT

VLHQDWLNGKEYKCKVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGNVFSCSVMHEALH

NHYTQKSLSLSPGKGGGGGGGGGGALCNCNRIIIPHQCWKKCGKK

FIG. 13

SEQ ID NO: 2

ASTKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSVLT
VLHQDWLNGKEYKCKVSNKALPAPIEKTISKAKGQPREPQVYTLPPSRDELTKNQVSLTCLVKG
FYPSDIAVEWESNGQPENNYKTTPPVLDSDGSFFLYSKLTVDKSRWQQGNVFSCSVMHEALH
NHYTQKSLSLSPGK<u>GGGGALCNCNRIIIPHQC</u>WKKCGK<u>KGGGGGGGGALCNCNRIIIPHQC</u>
<u>WKKCGKK</u>

FIG. 14

SEQ ID NO: 3

ASTKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSVLT
VLHQDWLNGKEYKCKVSNKALPAPIEKTISKAKGQPREPQVYTLPPSRDELTKNQVSLTCLVKG
FYPSDIAVEWESNGQPENNYKTTPPVLDSDGSFFLYSKLTVDKSRWQQGNVFSCSVMHEALH
NHYTQKSLSLSPGK

FIG. 15

PEPTIBODIES, COMPOSITIONS THEREOF, AND METHODS OF TREATING ATRIAL FIBRILLATION

CROSS-REFERENCE TO RELATED APPLICATIONS

This application is a continuation/continuation-in-part application under 35 U.S.C. § 111(a) of Patent Cooperation Treaty Application No.: PCT/US2017/064352, filed on Dec. 1, 2017, entitled "PEPTIBODIES, COMPOSITIONS THEREOF, AND METHODS OF TREATING ATRIAL FIBRILLATION," the contents of which is incorporated by reference herein in its entirety.

This application claims the benefit of and priority to U.S. Provisional Patent Application No. 62/428,749, filed on Dec. 1, 2016, entitled "PEPTIBODIES, COMPOSITIONS THEREOF, AND METHODS OF TREATING ATRIAL FIBRILLATION," the contents of which is incorporated by reference herein in its entirety.

STATEMENT REGARDING FEDERALLY SPONSORED RESEARCH OR DEVELOPMENT

This invention was made with government support HL129136 and HL130864 awarded by the National Institutes of Health. The Government has certain rights in the invention.

SEQUENCE LISTING

This application contains a sequence listing filed in electronic form as an ASCII.txt file entitled 292103-2800.txt, created on TBD. The content of the sequence listing is incorporated herein in its entirety.

BACKGROUND

Atrial fibrillation (AF) is the most common heart arrhythmia patients present with in the clinic. Chronic AF is particularly challenging to treat with currently available antiarrhythmics. As such there exists a need for improved compositions and method for treating AF.

SUMMARY

Described herein are peptibodies that can be composed of a first monomer and a second monomer, wherein each monomer can include an Fc polypeptide; a first TertiapinQ peptide, and wherein the N-terminus of the first TertiapinQ peptide can be linked to the C-terminus of the Fc polypeptide via a first linker; and wherein the first monomer and the second monomer can be attached via a disulfide bridge between the Fc polypeptide of the first monomer and the Fc polypeptide of the second monomer. The Fc polypeptide can be a human Fc polypeptide. The Fc polypeptide can have an amino acid sequence that is about 90%-100% identical to SEQ ID NO.: 3 or 9. The TertiapinQ peptide can have an amino acid sequence that is about 85%-100% identical to SEQ ID NO.: 4. The first linker can be a glycine linker. The first linker can be a glycine linker consisting of 5 glycine residues. The first monomer and the second monomer can each further include a second TertiapinQ peptide, wherein the N-terminus of the second TertiapinQ peptide can be linked to the C-terminus of the first TertiapinQ peptide via a second linker. The second TertiapinQ peptide can have an amino acid sequence that is about 85%-100% identical to SEQ ID NO.: 4. The second linker can be a glycine linker. The second linker can be a glycine linker consisting of 8 glycine residues.

Also described herein are pharmaceutical formulations that can include an amount of a peptibody as described herein and a pharmaceutically acceptable carrier. The peptibody can be composed of a first monomer and a second monomer, wherein each monomer can include an Fc polypeptide; a first TertiapinQ peptide, and wherein the N-terminus of the first TertiapinQ peptide can be linked to the C-terminus of the Fc polypeptide via a first linker; and wherein the first monomer and the second monomer can be attached via a disulfide bridge between the Fc polypeptide of the first monomer and the Fc polypeptide of the second monomer. The Fc polypeptide can be a human Fc polypeptide. The Fc polypeptide can have an amino acid sequence that is about 90%-100% identical to SEQ ID NO.: 3 or 9. The TertiapinQ peptide can have an amino acid sequence that is about 85%-100% identical to SEQ ID NO.: 4. The first linker can be a glycine linker. The first linker can be a glycine linker consisting of 5 glycine residues. The first monomer and the second monomer can each further include a second TertiapinQ peptide, wherein the N-terminus of the second TertiapinQ peptide can be linked to the C-terminus of the first TertiapinQ peptide via a second linker. The second TertiapinQ peptide can have an amino acid sequence that is about 85%-100% identical to SEQ ID NO.: 4. The second linker can be a glycine linker. The second linker can be a glycine linker consisting of 8 glycine residues. The amount of the pepdibody in the pharmaceutical formulation can be an amount effective to block $I_{KACh}$ current in an atrial myocyte. The amount of the peptidbody in the pharmaceutical formulation can be an amount effective to treat chronic atrial fibrillation or a symptom thereof in a subject in need thereof.

Also described herein are methods that can include the step of administering an amount of a peptibody or a pharmaceutical formulation as described herein to a subject in need thereof. The subject in need thereof can have chronic atrial fibrillation.

Also described herein are methods of treating chronic atrial fibrillation in a subject in need thereof that can include the step of administering an amount of a peptibody or a pharmaceutical formulation as described herein to a subject in need thereof. The subject in need thereof can have chronic atrial fibrillation.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 5A shows a side scatter plot of unlabeled cells. FIG. 5B shows a side scatter plot of cells labeled with 10 nM tertiapinQ-ATT0688. FIG. 5C shows a histogram of events from FIG. 5A and FIG. 5B, where the left histogram is that of unlabeled cells (UNL), and the histogram to the right is that of labeled cells (LBL). FIG. 5D shows a graph demonstrating a dose response curve of TertiapinQ fluorescence in the HEK cells. IC50=11 nM, hill coefficient=1.7, $R^2$=0.99.

FIGS. 8J and 8K show a time course of the average DF and singularity point (SP) density changes in 4 hearts. The X's along the X axis denote moment of AF termination.

FIGS. 10A-10B show graphs demonstrating that $APD_{75}$ and $APD_{50}$ measured in the optical mapping experiments at baseline (black) and after 200 nM TertiapinQ (grey). Four individual experiments are shown, and the bars denote the averages. *p<0.05, **p<0.01.

FIGS. 11A-11I show graphs of flow cytometry results that can demonstrate (FIGS. 11A-11C) negative control HEK293 cell stably expressing Kir3.1/3.4 (GIRK cells); (FIGS. 11D-11F) PE conjugated secondary antibody only; and (FIGS. 11G-11I) peptibody (about 0.01 µM) plus 2°-PE. FIGS. 11A, 11D, and 11G can demonstrate a gating strategy to select for single cells. FIGS. 11B, 11E, and 11H can show that the absence of DAPI staining was used to select live cells. FIGS. 11O, 11F, and 11I can show PE-fluorescence of a population of live, single cells.

FIG. 13 shows SEQ ID NO: 1.
FIG. 14 shows SEQ ID NO: 2.
FIG. 15 shows SEQ ID NO: 3.

DETAILED DESCRIPTION

Figure 1A:
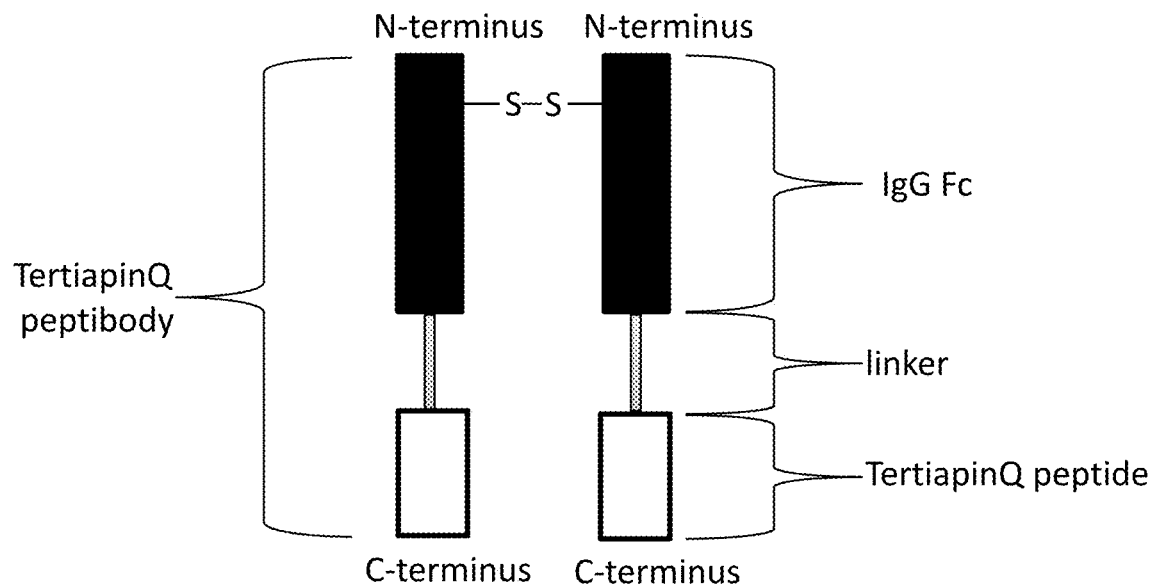
FIGS. 1A and 1B show embodiments of a TertiapinQ peptibody having one (FIG. 1A) or two (FIG. 1B) TertiapinQ peptides per IgG Fc monomer.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value and intervening range of values, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates and may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, biology, microbiology, nanotechnology, chemistry, organic chemistry, biochemistry, physiology, and the like, which are within the skill of the art. Such techniques are explained fully in the literature.

Definitions

As used herein, "about," "approximately," and the like, when used in connection with a numerical variable, can generally refers to the value of the variable and to all values of the variable that are within the experimental error (e.g., within the 95% confidence interval for the mean) or within +/−10% of the indicated value, whichever is greater.

As used herein, "active agent" or "active ingredient" can refer to a substance, compound, or molecule, which is biologically active or otherwise, induces a biological or physiological effect on a subject to which it is administered to. In other words, "active agent" or "active ingredient" refers to a component or components of a composition to which the whole or part of the effect of the composition is attributed.

As used herein, "additive effect" can refer to an effect arising between two or more molecules, compounds, substances, factors, or compositions that is equal to or the same as the sum of their individual effects.

As used herein, "antibody" can refer to a glycoprotein containing at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. Each light chain is comprised of a light chain variable region and a light chain constant region. The VH and VL regions retain the binding specificity to the antigen and can be further subdivided into regions of hypervariability, termed complementarity determining regions (CDR). The CDRs are interspersed with regions that are more conserved, termed framework regions (FR). Each VH and VL is composed of three CDRs and four framework regions, arranged from amino-terminus to carboxy-terminus in the following order: FR1, CDR1, FR2, CDR2, FR3, CDR3, and FR4. The variable regions of the heavy and light chains contain a binding domain that interacts with an antigen.

As used herein, "anti-infective" can refer to compounds or molecules that can either kill an infectious agent or inhibit it from spreading. Anti-infectives include, but are not limited to, antibiotics, antibacterials, antifungals, antivirals, and antiprotozoans.

As used herein, "aptamer" can refer to single-stranded DNA or RNA molecules that can bind to pre-selected targets including proteins with high affinity and specificity. Their specificity and characteristics are not directly determined by their primary sequence, but instead by their tertiary structure.

As used herein, "cDNA" can refer to a DNA sequence that is complementary to a RNA transcript in a cell. It is a man-made molecule. Typically, cDNA is made in vitro by an enzyme called reverse-transcriptase using RNA transcripts as templates.

As used herein, "concentrated" can refer to a molecule or population thereof, including but not limited to a polynucleotide, peptide, polypeptide, protein, antibody, or fragments thereof, that is distinguishable from its naturally occurring counterpart in that the concentration or number of molecules per volume is greater than that of its naturally occurring counterpart.

As used herein, "control" can refer to an alternative subject or sample used in an experiment for comparison purpose and included to minimize or distinguish the effect of variables other than an independent variable.

As used herein, "chemotherapeutic agent" or "chemotherapeutic" can refer to a therapeutic agent utilized to prevent or treat cancer.

As used herein, "chronic atrial fibrillation" is a term of art that can refer to atrial fibrillation that is continuously present, uninterrupted, for 7 days or more.

As used herein, "culturing" can refer to maintaining cells under conditions in which they can proliferate and avoid senescence as a group of cells. "Culturing" can also include conditions in which the cells also or alternatively differentiate.

As used herein, "deoxyribonucleic acid (DNA)" and "ribonucleic acid (RNA)" can generally refer to any polyribonucleotide or polydeoxribonucleotide, which may be unmodified RNA or DNA or modified RNA or DNA. RNA may be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), or ribozymes.

As used herein, "DNA molecule" can include nucleic acids/polynucleotides that are made of DNA.

As used herein, "derivative" can refer to any compound having the same or a similar core structure to the compound but having at least one structural difference, including substituting, deleting, and/or adding one or more atoms or functional groups. The term "derivative" does not mean that the derivative is synthesized from the parent compound either as a starting material or intermediate, although this may be the case. The term "derivative" can include prodrugs, or metabolites of the parent compound. Derivatives include compounds in which free amino groups in the parent compound have been derivatized to form amine hydrochlorides, p-toluene sulfoamides, benzoxycarboamides, t-butyloxycarboamides, thiourethane-type derivatives, trifluoroacetylamides, chloroacetylamides, or formamides. Derivatives include compounds in which carboxyl groups in the parent compound have been derivatized to form methyl and ethyl esters, or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imine, thiones, sulfones, tertiary amides, and sulfides. "Derivatives" also includes extensions of the replacement of the cyclopentane ring with saturated or unsaturated cyclohexane or other more complex, e.g., nitrogen-containing rings, and extensions of these rings with side various groups.

As used herein, "dose," "unit dose," or "dosage" can refer to physically discrete units suitable for use in a subject, each unit containing a predetermined quantity of the TertiapinQ peptibody and/or a pharmaceutical formulation thereof calculated to produce the desired response or responses in association with its administration.

As used herein, "effective amount" can refer to the amount of a compound provided herein that is sufficient to effect beneficial or desired biological, emotional, medical, or clinical response of a cell, tissue, system, animal, or human. An effective amount can be administered in one or more administrations, applications, or dosages. The term also includes within its scope amounts effective to enhance or restore to substantially normal physiological function. The "effective amount" can refer to the amount of a TertiapinQ peptibody provided herein that can reduce and/or block $I_{KACh}$ in vitro and/or in vivo. The "effective amount" can refer to the amount of a TertiapinQ peptibody provided herein that can reduce and/or block $I_{KACh}$ in vitro or in vivo while having minimal effects on the atrial action potential in a normal heart. The "effective amount" can refer to the amount of a TertiapinQ peptibody provided herein that can prolong action potential duration in atrial myocytes in a subject having chronic AF. The "effective amount" can refer to the amount of a TertiapinQ peptibody provided herein that can terminate cholinergic AF without affecting ventricular electrophysiology. The "effective amount" can refer to the amount of a TertiapinQ peptibody provided herein that can have an increased half-life when administered in vivo as compared to a TertiapinQ peptide alone. The "effective amount" can refer to the amount of a TertiapinQ peptibody provided herein that can treat chronic AF or a symptom thereof. The "effective amount" can refer to the amount of a TertiapinQ peptibody provided herein that can treat atrial arrhythmias or a symptom thereof.

As used herein, "expression" can refers to the process by which polynucleotides are transcribed into RNA transcripts. In the context of mRNA and other translated RNA species, "expression" also refers to the process or processes by which the transcribed RNA is subsequently translated into peptides, polypeptides, or proteins.

As used herein, the term "encode" can refer to principle that DNA can be transcribed into RNA, which can then be translated into amino acid sequences that can form proteins.

As used herein, the terms "Fc portion," "Fc region," and the like are used interchangeable herein and can refer to the fragment crystallizable region of an antibody that interacts with cell surface receptors called Fc receptors and some proteins of the complement system. The IgG Fc region is composed of two identical protein fragments that are derived from the second and third constant domains of the IgG antibody's two heavy chains.

As used herein, "gene" can refer to a hereditary unit corresponding to a sequence of DNA that occupies a specific location on a chromosome and that contains the genetic instruction for a characteristic(s) or trait(s) in an organism. The term gene can refer to both translated and untranslated regions of a subject's genome.

As used herein, "identity," is a relationship between two or more nucleotide or polypeptide sequences, as determined by comparing the sequences. In the art, "identity" also refers to the degree of sequence relatedness between nucleotide or polypeptide as determined by the match between strings of such sequences. "Identity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J. Applied Math. 1988, 48: 1073. Preferred methods to determine identity are designed to give the largest match between the sequences tested. Methods to determine identity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 1970, 48: 443-453,) algorithm (e.g., NBLAST, and XBLAST). The default parameters are used to determine the identity for the polypeptides of the present disclosure, unless stated otherwise.

As used herein, "immunomodulator," can refer to an agent, such as a therapeutic agent, which is capable of modulating or regulating one or more immune function or response.

As used herein, "isolated" means separated from constituents, cellular and otherwise, in which the polynucleotide, peptide, polypeptide, protein, antibody, or fragments thereof, are normally associated with in nature. A non-naturally occurring polynucleotide, peptide, polypeptide, protein, antibody, or fragments thereof, do not require "isolation" to distinguish it from its naturally occurring counterpart.

As used herein, "mammal," for the purposes of treatments, can refer to any animal classified as a mammal, including human, domestic and farm animals, nonhuman primates, and zoo, sports, or pet animals, such as, but not limited to, dogs, horses, cats, and cows.

The term "molecular weight", as used herein, can generally refer to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

As used herein, "negative control" can refer to a "control" that is designed to produce no effect or result, provided that all reagents are functioning properly and that the experiment is properly conducted. Other terms that are interchangeable with "negative control" include "sham," "placebo," and "mock."

As used herein, "nucleic acid" and "polynucleotide" generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein. "Polynucleotide" and "nucleic acids" also includes PNAs (peptide nucleic acids), phosphorothioates, and other variants of the phosphate backbone of native nucleic acids. Natural nucleic acids have a phosphate backbone, artificial nucleic acids may contain other types of backbones, but contain the same bases. Thus, DNAs or RNAs with backbones modified for stability or for other reasons are "nucleic acids" or "polynucleotide" as that term is intended herein.

As used herein, "nucleic acid sequence" and "oligonucleotide" also encompasses a nucleic acid and polynucleotide as defined above. As used herein, "organism", "host", and "subject" refers to any living entity comprised of at least one cell. A living organism can be as simple as, for example, a single isolated eukaryotic cell or cultured cell or cell line, or as complex as a mammal, including a human being, and animals (e.g., vertebrates, amphibians, fish, mammals, e.g., cats, dogs, horses, pigs, cows, sheep, rodents, rabbits, squirrels, bears, primates (e.g., chimpanzees, gorillas, and humans). "Subject" may also be a cell, a population of cells, a tissue, an organ, or an organism, preferably to human and constituents thereof.

As used herein, "overexpressed" or "overexpression" can refer to an increased expression level of an RNA or protein product encoded by a gene as compared to the level of expression of the RNA or protein product in a normal or control cell.

As used herein, "operatively linked" can indicate that the regulatory sequences useful for expression of the coding sequences of a nucleic acid are placed in the nucleic acid molecule in the appropriate positions relative to the coding sequence so as to effect expression of the coding sequence. This same term can be applied to the arrangement of coding sequences and/or transcription control elements (e.g. promoters, enhancers, and termination elements), and/or selectable markers in an expression vector. "Operatively linked" can also refer to an indirect attachment (i.e. not a direct fusion) of two or more polynucleotide sequences or polypeptides to each other via a linking molecule (also referred to herein as a linker).

As used herein, "patient" refers to an organism, host, or subject in need of treatment.

As used herein "peptide" refers to chains of at least 2 amino acids that are short, relative to a protein or polypeptide.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" can refer to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "pharmaceutically acceptable salt" can refer to any acid or base addition salt whose counter-ions are non-toxic to the subject to which they are administered in pharmaceutical doses of the salts.

As used herein, "plasmid" as used herein can refer to a non-chromosomal double-stranded DNA sequence including an intact "replicon" such that the plasmid is replicated in a host cell.

As used herein, "positive control" can refer to a "control" that is designed to produce the desired result, provided that all reagents are functioning properly and that the experiment is properly conducted.

As used herein, "preventative" and "prevent" can refer to hindering or stopping a disease or condition before it occurs, even if undiagnosed, or while the disease or condition is still in the sub-clinical phase.

As used herein, "protein" as used herein can refer to a molecule composed of one or more chains of amino acids in a specific order. The term protein is used interchangeable with "polypeptide." The order is determined by the base sequence of nucleotides in the gene coding for the protein. Proteins are required for the structure, function, and regulation of the body's cells, tissues, and organs.

As used herein, "purified" or "purify" can be used in reference to a nucleic acid sequence, peptide, or polypeptide that has increased purity relative to the natural environment.

As used herein, the term "recombinant" or "engineered" can generally refer to a non-naturally occurring nucleic acid, nucleic acid construct, or polypeptide. Such non-naturally occurring nucleic acids may include natural nucleic acids that have been modified, for example that have deletions, substitutions, inversions, insertions, etc., and/or combinations of nucleic acid sequences of different origin that are joined using molecular biology technologies (e.g., a nucleic acid sequences encoding a fusion protein (e.g., a protein or polypeptide formed from the combination of two different proteins or protein fragments), the combination of a nucleic acid encoding a polypeptide to a promoter sequence, where the coding sequence and promoter sequence are from different sources or otherwise do not typically occur together naturally (e.g., a nucleic acid and a constitutive promoter), etc. Recombinant or engineered can also refer to the polypeptide encoded by the recombinant nucleic acid. Non-naturally occurring nucleic acids or polypeptides include nucleic acids and polypeptides modified by man.

As used herein, "separated" can refer to the state of being physically divided from the original source or population such that the separated compound, agent, particle, or molecule can no longer be considered part of the original source or population.

As used interchangeably herein, "subject," "individual," or "patient" can refer to a vertebrate organism, such as a mammal (e.g. human).

As used herein, "substantially pure" can mean an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

As used herein, "therapeutic" can refer to treating, healing, and/or ameliorating a disease, disorder, condition, or side effect, or to decreasing in the rate of advancement of a disease, disorder, condition, or side effect. A "therapeutically effective amount" can therefore refer to an amount of a compound that can yield a therapeutic effect.

As used herein, "TertiapinQ peptide" can refer to any peptide that is about 90-100% identical to SEQ ID NO.: 4.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as AF, particularly chronic AF. The effect can be therapeutic in terms of a partial or complete cure of a disease, condition, symptom or adverse effect attributed to the disease, disorder, or condition. The term "treatment" as used herein covers any treatment of AF, particularly chronic AF, in a mammal, particularly a human, and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented.

As used herein, "variant" refers to a polypeptide that differs from a reference polypeptide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally. "Variant" includes functional and structural variants.

As used herein, the term "vector" or is used in reference to a vehicle used to introduce an exogenous nucleic acid sequence into a cell. A vector may include a DNA molecule, linear or circular (e.g. plasmids), which includes a segment encoding a polypeptide of interest operatively linked to additional segments that provide for its transcription and translation upon introduction into a host cell or host cell organelles. Such additional segments may include promoter and terminator sequences, and may also include one or more origins of replication, one or more selectable markers, an enhancer, a polyadenylation signal, etc. Expression vectors are generally derived from yeast or bacterial genomic or plasmid DNA, or viral DNA, or may contain elements of both.

Unless otherwise defined herein, all technical and scientific terms used herein have the same meaning as commonly understood by one of ordinary skill in the art.

Discussion

AF is the most common arrhythmia observed in clinical practice. The prevalence of AF in the general population is greater than about 1%, of which about 70% of the people with AF are 65 years or older. Thus, AF is increasingly recognized as a disease of age and is associated with increased morbidity and mortality. It has been found that AF independently increases mortality, is associated with dementia and Alzheimer's disease, and is a considered a major risk factor for stroke.

The treatment of chronic AF remains inadequate, particularly as the disease slowly progresses from paroxysmal to the chronic stages that include persistent, longstanding, and permanent AF. Clinical studies have demonstrated that antiarrhythmics or ablation strategies do not result in complete freedom from AF, especially chronic AF. Antiarrhythmic drug therapy remains the first line of defense. However, the rate of conversion to sinus rhythm in AF achieved with current antiarrhythmics is only 25%-60% depending on the particular agent and study. Moreover, current antiarrhythmic agents are inadequate, generally non-specific, and carry risks of severe adverse effects. Maintenance of sinus rhythm with antiarrhythmics offers secondary end point benefits such as improvement in left ventricular function, walking distance, in addition to atrial size reduction. Hence, there is need for an improved antiarrhythmic armamentarium for treatment of AF, particularly chronic AF.

With these deficiencies in mind, described herein are engineered peptibodies that can be capable of blocking the acetylcholine activated inward rectifier potassium current ($I_{KACh}$). In some embodiments, the peptibody can include a TertiapinQ peptide fused and/or operatively linked to an IgG1 Fc antibody fragment. The peptibodies and formulations thereof described herein can be capable of treating AF or symptoms thereof in a subject in need thereof. Also provided herein are formulations that can include the peptibodies provided herein and methods of administering the peptibodies and formulations thereof to a subject in need thereof. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

TertiapinQ Peptibodies

Remodeling in the chronically fibrillating atria is complex. AF is a disease that occurs in stages over time with, transcriptional to post-translational remodeling of the cells and atrial tissue occurring over the progression of the disease. Additionally, autonomic, anatomical, sarcolemmal, and subsarcolemmal electrophysiological remodeling is observed with chronic AF and results in aberrant electrical propagation changes, shortening of the effective refractory period and abnormal excitation-contraction coupling. For instance, increased fibrosis, decreased intracellular coupling, reduced $I_{Na}$, $I_{CaL}$, increased $I_{Kur}$, in addition to mitochondrial and calcium handling abnormalities are observed with the disease.

It has been demonstrated in humans with chronic AF and in animal models of chronic AF, that the inward rectifier potassium current ($I_{KACh}$) is remodeled. $I_{KACh}$ is a current that flows through tetrameric sarcolemmal channels formed by the proteins Kir3.1 and Kir3.4. In normal baseline physiology, $I_{KACh}$ activity is minimal. Upon parasympathetic stimulation, acetylcholine binds to the muscarinic (M2) G-protein coupled receptor, which results in the $G_{\beta\gamma}$ subunit to bind Kir3.1 and kir3.4. Upon binding the $G_{\beta\gamma}$ subunit, Kir3.1 and Kir3.4 undergo a conformational change, which promotes their interaction with phosphatidylinositol bisphosphate ($PIP_2$) and channel activation.

As $I_{KACh}$ is important in heart rate modulation, in individuals without AF the on/off switching of the current is tightly regulated. However in individuals with chronic AF, $I_{KACh}$ is constitutively active, irrespective of parasympathetic stimulation. This may be due to PKCε phosphorylation of Kir3.1. This dysregulation ultimately leads to a net increase in background inward rectifier current and shortening of the APD (action potential duration) and the subsequent formation of stable electrical rotors which activate the myocardium at high frequencies. This activation of the myocardium can then lead to fibrillation.

It has been reported that some compounds (e.g. NTC-801, a benzopyrene derivative, and AZD2927, a benzamide related compound) can selectively inhibit $I_{KACh}$ at submicromolar concentrations. However, these drugs failed to revert paroxysmal AF and atrial flutter, respectively, in patients (Podd et al., Europace: European pacing, arrhythmias, and cardiac electrophysiology: journal of the working groups on cardiac pacing, arrhythmias, and cardiac cellular electrophysiology of the European Society of Cardiology. 2015; and Walfridsson et al., Europace: European pacing, arrhythmias, and cardiac electrophysiology: journal of the working groups on cardiac pacing, arrhythmias, and cardiac cellular electrophysiology of the European Society of Cardiology. 2015; 17:473-482). Further several Class I and III antiarrhythmics have been demonstrated to fail at blocking ca-$I_{KACh}$.

TertiapinQ is an approximately 21 amino acid peptide variant of Tertiapin that was initially isolated from European honey bee venom and can block $I_{KACh}$. TertiapinQ was observed to (1) inhibit constitutively active $I_{KACh}$ while having only minor effects on the atrial action potential in a normal heart; (2) prolong action potential duration in atrial myocytes from patients with chronic AF; and (3) terminate cholinergic AF without affecting ventricular electrophysiology. Despite these promising effects the use of the peptide alone has been limited possibly due to issues with administration and metabolism of such a small (about 21 amino acid) peptide.

Described herein are TertiapinQ peptibodies that can include at least two monomers that are each composed of at least one TertiapinQ peptide fused and/or operatively linked to an IgG Fc monomer at the C-terminus of the IgG Fc monomer. It will be instantly appreciated that each TertiapinQ peptibody can be composed of two monomers that dimerize via a disulfide bridge between the two IgG Fc monomer fragments. The TertiapinQ peptibodies described herein can be capable of reducing and/or blocking $I_{KACh}$. The TertiapinQ peptibodies described herein can be capable of reducing and/or blocking $I_{KACh}$ while having minimal effects on the atrial action potential in a normal heart. The TertiapinQ peptibodies described herein can be capable of prolonging action potential duration in atrial myocytes in a patient having chronic AF. The TertiapinQ peptibodies described herein can be capable of terminating cholinergic AF without effecting ventricular electrophysiology. The TertiapinQ peptibodies described herein can have an increased half-life when administered in vivo as compared to a TertiapinQ peptide alone.

Figure 1B:
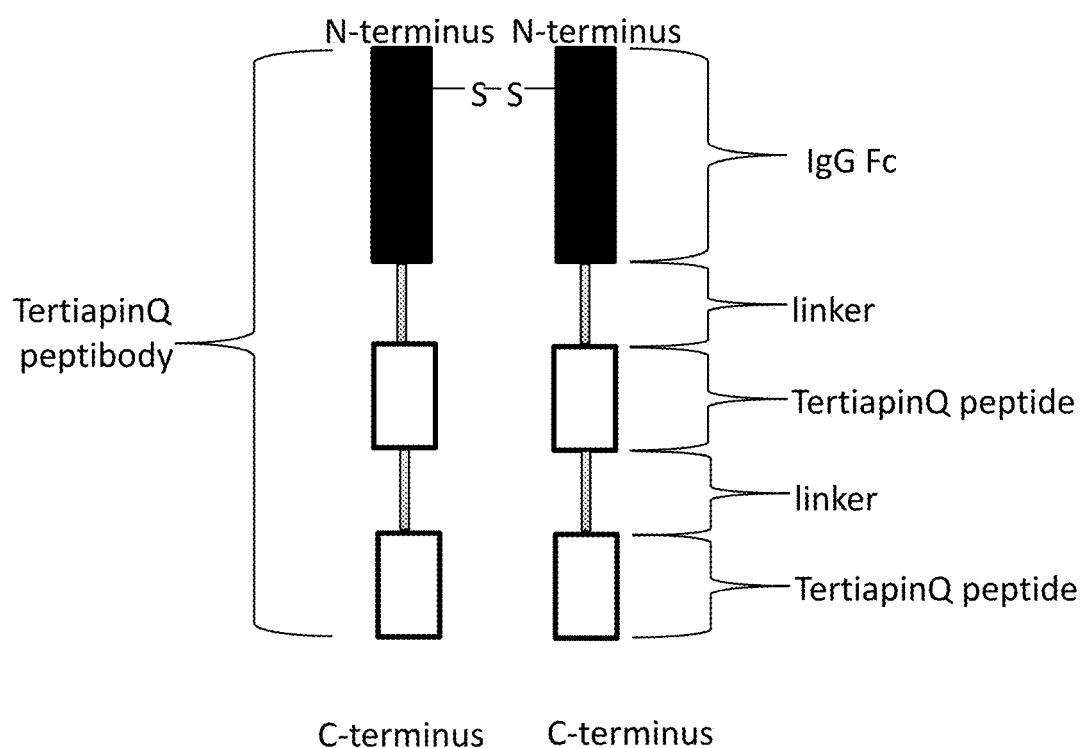

FIGS. 1A and 1B show a TertiapinQ peptibody having one (FIG. 1A) or two (FIG. 1B) TertiapinQ peptides per IgG Fc monomer. As shown in FIG. 1A, each IgG Fc monomer can be fused and/or operatively linked to a single TertiapinQ peptide at the C-terminus of each of the IgG Fc monomer. In some embodiments, the TertiapinQ peptide can be directly fused to the C-terminus of the IgG Fc monomer (not shown in FIG. 1A). In other words, in some embodiments, there are no other amino acids between the C-terminal amino acid of the IgG Fc monomer and the N-terminal amino acid of the TertiapinQ peptide. As shown in FIG. 1A, the TertiapinQ peptide can be operatively linked via an amino acid linker to the C-terminus of the IgG Fc monomer. The linker can be a glycine linker having between 5 and 20 glycine residues. Additional suitable linkers can be made from a number of different amino acid combinations. In some embodiments, the linkers can be composed of a majority of glycine residues. The linkers can have a one or more alanines, serines, or threonines in any position within the linker. The exact sequences and number of residues in the linker can be varied. In some embodiments, the linker can be composed of 5 glycine residues. The N-terminus of the TertiapinQ peptide then can be fused to the C-terminal residue of the linker.

Each IgG Fc monomer can be an IgG1 Fc monomer. The Fc monomer can be modified to enhance binding to the FcRn (neonatal Fc receptor) to enhance plasma half-life (Dall'Acqua W F, Kiener P A, Wu H. Properties of human IgG1s engineered for enhanced binding to the neonatal Fc receptor (FcRn) J Biol Chem. 2006; 281:23514-23524.). The Fc monomer can be modified to decrease binding to stimulatory FcγRs to prevent activation of leukocytes. In the alternate, each IgG Fc monomer can be an IgG2 or IgG4 Fc monomer.

In some embodiments, the TertiapinQ peptibody can have two or more TertiapinQ peptides operatively linked and/or fused to the C-terminus of each IgG Fc monomer. In some embodiments, one or more of the TertiapinQ peptides can be directly fused to the C-terminus of each IgG Fc monomer and/or other TertiapinQ peptides (not shown in FIG. 1B). In some embodiments a first TertiapinQ peptide can be operatively linked via a first linker to the C-terminus of each IgG Fc monomer. A second TertiapinQ peptide can be operatively linked to the first TertiapinQ peptide via a second linker. The first TertiapinQ peptide can be the same as the second TertiapinQ peptide or the first TertiapinQ peptide can be a different TertiapinQ peptide as the second TertiapinQ peptide. The first linker can be the same as the second linker or the first linker can be different from the second linker. The first linker and/or the second linker can be a glycine linker having between 5 and 20 glycine residues. The linker can be a glycine linker having between 5 and 20 glycine residues. Suitable linkers can be made from a number of different amino acid combinations. In embodiments, the linkers can be composed of a majority of glycine residues. The linkers can have a one or more alanines, serines, or threonines in any position within the linker. The exact sequences and number of residues in the linker can be varied. In some embodiments, the linker can be composed of 5 glycine residues. In some embodiments, the first linker and/or the second linker can be composed of 5 glycine residues. In some embodiments, the first linker can be a linker composed of 5 glycine residues and the second linker can be composed of 8 glycine residues.

Each IgG Fc monomer can be an IgG1 Fc monomer. The Fc monomer can be modified to enhance binding to the FcRn (neonatal Fc receptor) to enhance plasma half-life (Dall'Acqua W F, Kiener P A, Wu H. Properties of human IgG1s engineered for enhanced binding to the neonatal Fc receptor (FcRn) J Biol Chem. 2006; 281:23514-23524). The Fc monomer can be modified to decrease binding to stimulatory FcγRs to prevent activation of leukocytes. In the alternate, each IgG Fc monomer can be an IgG2 or IgG4 Fc monomer.

The IgG Fc monomer can have an amino acid sequence that can be about 90-100% identical to SEQ ID NO.: 3 or 9. SEQ ID NO 3 is also shown in FIG. 15, where the underlines indicates residues that can be involved in disulfide bridge formation with other Fc monomers. In some embodiments, the IgG Fc monomer can be about 95% identical to SEQ ID NO.: 3 or 9. Any of the TertiapinQ peptides that are included in the TertiapinQ peptibody can have an amino acid sequence that can be about 85-100% identical to SEQ ID NO.: 4.

Each monomer of the TertiapinQ peptibody can have an amino acid sequence that can be about 90-100% identical to any one of SEQ ID NOs: 1 or 2. The single underlined region(s) in SEQ ID NOs.: 1 and 2 indicate the amino acid residues corresponding to the linker(s) (FIGS. 13-14). The double underlined and italicized region(s) of SEQ ID NOs.: 1 and 2 indicate the amino acid residues of the TertiapinQ peptides (FIGS. 13 and 14). The non-underlined and non-italicized region in SEQ ID NOs.: 1 and 2 indicates the amino acid residues of the IgG Fc monomer. It will be appreciated that this disclosure encompasses addition full sequences for the TertiapinQ peptibodies that are not limited to SEQ ID NOs.: 1 and 2 based at least on the variations of the different components of the TertiapinQ peptibody provided and described herein.

Also described herein are nucleic acid sequences that can encode any of the polypeptide and peptide sequences provided herein. The nucleic acid sequences can be a DNA sequence, cDNA sequence, and RNA sequences. One of ordinary skill in the art will appreciate corresponding nucleic acid sequences if provided only one form. For example, if provided a cDNA sequence, one of ordinary skill in the art will instantly appreciate the corresponding RNA and polypeptide sequences.

In some embodiments, the cDNA sequence of the TertiapinQ peptibody can be about 80-100% identical to any one of SEQ ID NOs.: 5-8. The cDNA sequence can be codon optimized for expression in a particular cell types. For example, the cDNA sequence of the TertiapinQ peptibody or any particular portion thereof can be codon optimized for expression in a bacterial cell, such as E. coli, or a mammalian cell, such as a human cell. In some embodiments, the codon optimization at the nucleotide level does not result in a change in the polypeptide sequence but can improve expression and/or replication in a particular cell type, which can be useful for production of the polypeptide.

Any of the cDNA sequences described herein can be incorporated into a suitable expression vector. The expression vector can contain one or more regulatory sequences or one or more other sequences used to facilitate the expression of the TertiapinQ peptibody. The expression vector can contain one or more regulatory sequences and/or one or more other sequences used to facilitate the replication of the TertiapinQ peptibody expression vector. The expression vector can be suitable for expressing the TertiapinQ peptibody in a bacterial cell. In other embodiments, the expression vector can be suitable for expressing the TertiapinQ peptibody in a yeast cell. In further embodiments, the expression vector can be suitable for expressing the TertiapinQ peptibody in a plant cell. In other embodiments, the expression vector can be suitable for expressing the TertiapinQ peptibody in a mammalian cell. In another embodiment, the vector can be suitable for expressing the TertiapinQ peptibody in a fungal cell. In further embodiments, the vector can be suitable for expressing the TertiapinQ peptibody in an insect cell. Suitable expression vectors are generally known to those of ordinary skill in the art. The TertiapinQ peptibodies can be produced from an in vitro production system, which are generally known in the art.

TertiapinQ Peptibody Formulations

Also within the scope of this disclosure are pharmaceutical formulations that can contain an amount of a TertiapinQ peptibody as described elsewhere herein. The TertiapinQ peptibodies described herein can be provided to a subject in need thereof alone or as such as an active ingredient, in a pharmaceutical formulation. In some embodiments, the pharmaceutical formulations contain an effective amount of a TertiapinQ peptibody. The pharmaceutical formulations described herein can be administered to a subject in need thereof. The subject in need thereof can have AF, such as chronic AF. In some embodiments, the subject can be a human. In other embodiments, the TertiapinQ peptibody can be used in the manufacture of a medicament for the treatment or prevention of AF, such as chronic AF in a subject. The term pharmaceutical formulation also encompasses pharmaceutically acceptable salts of the pharmaceutical formulations and/or active ingredients provided herein.

Pharmaceutically Acceptable Carriers and Auxiliary Ingredients and Agents

The pharmaceutical formulations containing an effective amount of a TertiapinQ peptibody described herein can further include a pharmaceutically acceptable carrier. Suitable pharmaceutically acceptable carriers include, but are not limited to, water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active composition.

In addition to the effective amount of a TertiapinQ peptibody described herein, the pharmaceutical formulation can also include an effective amount of an auxiliary active agent, including but not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, chemotherapeutics, antihypertensives, anticoagulants, and antiarrhythmics.

Suitable hormones include, but are not limited to, aminoacid derived hormones (e.g. melatonin and thyroxine), small peptide hormones and protein hormones (e.g. thyrotropin-releasing hormone, vasopressin, insulin, growth hormone, luteinizing hormone, follicle-stimulating hormone, and thyroid-stimulating hormone), eiconsanoids (e.g. arachidonic acid, lipoxins, and prostaglandins), and steroid hormones (e.g. estradiol, testosterone, tetrahydro testosteron cortisol).

Suitable immunomodulators include, but are not limited to, prednisone, azathioprine, 6-MP, cyclosporine, tacrolimus, methotrexate, interleukins (e.g. IL-2, IL-7, and IL-12), cytokines (e.g. interferons (e.g. IFN-α, IFN-β, IFN-ε, IFN-κ, IFN-ω, and IFN-γ), granulocyte colony-stimulating factor, and imiquimod), chemokines (e.g. CCL3, CCL26 and CXCL7), cytosine phosphate-guanosine, oligodeoxynucleotides, glucans, antibodies, and aptamers).

Suitable antipyretics include, but are not limited to, non-steroidal anti-inflammants (e.g. ibuprofen, naproxen, ketoprofen, and nimesulide), aspirin and related salicylates (e.g. choline salicylate, magnesium salicylae, and sodium salicaylate), paracetamol/acetaminophen, metamizole, nabumetone, phenazone, and quinine.

Suitable anxiolytics include, but are not limited to, benzodiazepines (e.g. alprazolam, bromazepam, chlordiazepoxide, clonazepam, clorazepate, diazepam, flurazepam, lorazepam, oxazepam, temazepam, triazolam, and tofisopam), serotenergic antidepressants (e.g. selective serotonin reuptake inhibitors, tricyclic antidepresents, and monoamine oxidase inhibitors), mebicar, afobazole, selank, bromantane, emoxypine, azapirones, barbiturates, hydroxyzine, pregabalin, validol, and beta blockers.

Suitable antipsychotics include, but are not limited to, benperidol, bromoperidol, droperidol, haloperidol, moperone, pipaperone, timiperone, fluspirilene, penfluridol, pimozide, acepromazine, chlorpromazine, cyamemazine, dizyrazine, fluphenazine, levomepromazine, mesoridazine, perazine, pericyazine, perphenazine, pipotiazine, prochlorperazine, promazine, promethazine, prothipendyl, thioproperazine, thioridazine, trifluoperazine, triflupromazine, chlorprothixene, clopenthixol, flupentixol, tiotixene, zuclopenthixol, clotiapine, loxapine, prothipendyl, carpipramine, clocapramine, molindone, mosapramine, sulpiride, veralipride, amisulpride, amoxapine, aripiprazole, asenapine, clozapine, blonanserin, iloperidone, lurasidone, melperone, nemonapride, olanzaprine, paliperidone, perospirone, quetiapine, remoxipride, risperidone, sertindole, trimipramine, ziprasidone, zotepine, alstonie, befeprunox, bitopertin, brexpiprazole, cannabidiol, cariprazine, pimavanserin, pomaglumetad methionil, vabicaserin, xanomeline, and zicronapine.

Suitable analgesics include, but are not limited to, paracetamol/acetaminophen, non-steroidal anti-inflammants (e.g. ibuprofen, naproxen, ketoprofen, and nimesulide), COX-2 inhibitors (e.g. rofecoxib, celecoxib, and etoricoxib), opioids (e.g. morphine, codeine, oxycodone, hydrocodone, dihydromorphine, pethidine, buprenorphine), tramadol, norepinephrine, flupiretine, nefopam, orphenadrine, pregabalin, gabapentin, cyclobenzaprine, scopolamine, methadone, ketobemidone, piritramide, and aspirin and related salicylates (e.g. choline salicylate, magnesium salicylate, and sodium salicylate).

Suitable antispasmodics include, but are not limited to, mebeverine, papverine, cyclobenzaprine, carisoprodol, orphenadrine, tizanidine, metaxalone, methodcarbamol, chlorzoxazone, baclofen, dantrolene, baclofen, tizanidine, and dantrolene.

Suitable anti-inflammatories include, but are not limited to, prednisone, non-steroidal anti-inflammants (e.g. ibuprofen, naproxen, ketoprofen, and nimesulide), COX-2 inhibitors (e.g. rofecoxib, celecoxib, and etoricoxib), and immune selective anti-inflammatory derivatives (e.g. submandibular gland peptide-T and its derivatives).

Suitable anti-histamines include, but are not limited to, $H_1$-receptor antagonists (e.g. acrivastine, azelastine, bilastine, brompheniramine, buclizine, bromodiphenhydramine, carbinoxamine, cetirizine, chlorpromazine, cyclizine, chlorpheniramine, clemastine, cyproheptadine, desloratadine, dexbromapheniramine, dexchlorpheniramine, dimenhydrinate, dimetindene, diphenhydramine, doxylamine, ebasine, embramine, fexofenadine, hydroxyzine, levocetirzine, loratadine, meclozine, mirtazapine, olopatadine, orphenadrine, phenindamine, pheniramine, phenyltoloxamine, promethazine, pyrilamine, quetiapine, rupatadine, tripelennamine, and triprolidine), $H_2$-receptor antagonists (e.g. cimetidine, famotidine, lafutidine, nizatidine, rafitidine, and roxatidine), tritoqualine, catechin, cromoglicate, nedocromil, and β2-adrenergic agonists.

Suitable anti-infectives include, but are not limited to, amebicides (e.g. nitazoxanide, paromomycin, metronidazole, tinidazole, chloroquine, miltefosine, amphotericin b, and iodoquinol), aminoglycosides (e.g. paromomycin, tobramycin, gentamicin, amikacin, kanamycin, and neomycin), anthelmintics (e.g. pyrantel, mebendazole, ivermectin, praziquantel, abendazole, thiabendazole, oxamniquine), antifungals (e.g. azole antifungals (e.g. itraconazole, fluconazole, posaconazole, ketoconazole, clotrimazole, miconazole, and voriconazole), echinocandins (e.g. caspofungin, anidulafungin, and micafungin), griseofulvin, terbinafine, flucytosine, and polyenes (e.g. nystatin, and amphotericin b), antimalarial agents (e.g. pyrimethamine/sulfadoxine, artemether/lumefantrine, atovaquone/proquanil, quinine, hydroxychloroquine, mefloquine, chloroquine, doxycycline, pyrimethamine, and halofantrine), antituberculosis agents (e.g. aminosalicylates (e.g. aminosalicylic acid), isoniazid/rifampin, isoniazid/pyrazinamide/rifampin, bedaquiline, isoniazid, ethambutol, rifampin, rifabutin, rifapentine, capreomycin, and cycloserine), antivirals (e.g. amantadine, rimantadine, abacavir/lamivudine, emtricitabine/tenofovir, cobicistat/elvitegravir/emtricitabine/tenofovir, efavirenz/emtricitabine/tenofovir, avacavir/lamivudine/zidovudine, lamivudine/zidovudine, emtricitabine/tenofovir, emtricitabine/opinavir/ritonavir/tenofovir, interferon alfa-2v/ribavirin, peginterferon alfa-2b, maraviroc, raltegravir, dolutegravir, enfuvirtide, foscarnet, fomivirsen, oseltamivir, zanamivir, nevirapine, efavirenz, etravirine, rilpivirine, delaviridine, nevirapine, entecavir, lamivudine, adefovir, sofosbuvir, didanosine, tenofovir, avacivr, zidovudine, stavudine, emtricitabine, xalcitabine, telbivudine, simeprevir, boceprevir, telaprevir, lopinavir/ritonavir, fosamprenvir, dranuavir, ritonavir, tipranavir, atazanavir, nelfinavir, amprenavir, indinavir, sawuinavir, ribavirin, valcyclovir, acyclovir, famciclovir, ganciclovir, and valganciclovir), carbapenems (e.g. doripenem, meropenem, ertapenem, and cilastatin/imipenem), cephalosporins (e.g. cefadroxil, cephradine, cefazolin, cephalexin, cefepime, ceflaroline, loracarbef, cefotetan, cefuroxime, cefprozil, loracarbef, cefoxitin, cefaclor, ceftibuten, ceftriaxone, cefotaxime, cefpodoxime, cefdinir, cefixime, cefditoren, cefizoxime, and ceftazidime), glycopeptide antibiotics (e.g. vancomycin, dalbavancin, oritavancin, and telvancin), glycylcyclines (e.g. tigecycline), leprostatics (e.g. clofazimine and thalidomide), lincomycin and derivatives thereof (e.g. clindamycin and lincomycin), macrolides and derivatives thereof (e.g. telithromycin, fidaxomicin, erthromycin, azithromycin, clarithromycin, dirithromycin, and troleandomycin), linezolid, sulfamethoxazole/trimethoprim, rifaximin, chloramphenicol, fosfomycin, metronidazole, aztreonam, bacitracin, penicillins (amoxicillin, ampicillin, bacampicillin, carbenicillin, piperacillin, ticarcillin, amoxicillin/clavulanate, ampicillin/sulbactam, piperacillin/tazobactam, clavulanate/ticarcillin, penicillin, procaine penicillin, oxaxillin, dicloxacillin, and nafcillin), quinolones (e.g. lomefloxacin, norfloxacin, ofloxacin, qatifloxacin, moxifloxacin, ciprofloxacin, levofloxacin, gemifloxacin, moxifloxacin, cinoxacin, nalidixic acid, enoxacin, grepafloxacin, gatifloxacin, trovafloxacin, and sparfloxacin), sulfonamides (e.g. sulfamethoxazole/trimethoprim, sulfasalazine, and sulfasoxazole), tetracyclines (e.g. doxycycline, demeclocycline, minocycline, doxycycline/salicyclic acid, doxycycline/omega-3 polyunsaturated fatty acids, and tetracycline), and urinary anti-infectives (e.g. nitrofurantoin, methenamine, fosfomycin, cinoxacin, nalidixic acid, trimethoprim, and methylene blue).

Suitable chemotherapeutics include, but are not limited to, paclitaxel, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositumomab, carmustine, bleomycin, bosutinib, busulfan, alemtuzumab, irinotecan, vandetanib, bicalutamide, lomustine, daunorubicin, clofarabine, cabozantinib, dactinomycin, ramucirumab, cytarabine, cytoxan, cyclophosphamide, decitabine, dexamethasone, docetaxel, hydroxyurea, decarbazine, leuprolide, epirubicin, oxaliplatin, asparaginase, estramustine, cetuximab, vismodegib, asparginase Erwinia chrysanthemi, amifostine, etoposide, flutamide, toremifene, fulvestrant, letrozole, degarelix, pralatrexate, methotrexate, floxuridine, obinutuzumab, gemcitabine, afatinib, imatinib mesylatem, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, ado-trastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, prednisone, aldesleukin, mercaptopurine, zoledronic acid, lenalidomide, rituximab, octretide, dasatinib, regorafenib, histrelin, sunitinib, siltuximab, omacetaxine, thioguanine (tioguanine), dabrafenib, erlotinib, bexarotene, temozolomide, thiotepa, thalidomide, BCG, temsirolimus, bendamustine hydrochloride, triptorelin, aresnic trioxide, lapatinib, valrubicin, panitumumab, vinblastine, bortezomib, tretinoin, azacitidine, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, and all-trans retinoic acid.

Suitable anti-hypertensives include, but are not limited to, Bumetanide, furosemide, torsemide, epitizide, hydrochlorothiazide, chlorothiazide, bendroflumethiazide, indapamide, chlorthalidone, metolazone, amiloride, triamterene, spironolactone, amlodipine, cilnidipine, felodipine, isradipine, lercanidipine, levamlodipine, nicardipine, nifedipine, nimodipine, nitrendipine, diltiazem, verapamil, captopril, enalapril, fosinopril, lisinopril, perindopril, quinapril, ramipril, trandolapril, benazepril, candesartan, eprosartan, irbesartan, losartan, olmesartan, telmisartan, valsartan, fimasartan, atenolol, metoprolol, nadolol, nebivolol, oxprenolol, pindolol, propranolol, timolol, doxazosin, phentolamine, indoramin, phenoxybenzamine, prazosin, terazosin, tolazoline, bucindolol, carvedilol, and labetalol.

Suitable anticoagulants include but are not limited to, warfarin, dabigatran, apixaban, and rivaroxaban.

Suitable anti-arrhythmics include, but are not limited to, quinidine, ajmaline, procainamide, disopyramide, lidocaine, phenytoin, mexiletine, tocainide, encainide, flecainide, propafenone, moricizine, carvedilol, propranolol, esmolol, timolol, metoprolol, atenolol, bisoprolol, nebivolol, amiodarone, sotalol, ibutilide, dofetilide, dronedarone, verapamil, diltiazem, adenosine, digoxin, and magnesium sulfate.

Effective Amounts of the TertiapinQ Peptibodies and Auxiliary Agents

The pharmaceutical formulations can contain an effective amount of a TertiapinQ peptibody, and optionally, a therapeutically effective amount of an auxiliary agent. In some embodiments, the effective amount of the TertiapinQ peptibody can range from about 0.3 mg/kg bodyweight to about 30 mg/kg. The effective amount of the TertiapinQ peptibody can range from about 1 mg to about 10 g. For liquid formulations, some embodiments, the effective amount of the TertiapinQ peptibody or pharmaceutical formulation containing a TertiapinQ peptibody can range from about 10 μL to about 10 mL. One of skill in the art will appreciate that the exact volume will depend on, inter alia, the age and size of the subject, as well as the location of administration. The effective concentration of the TertiapinQ peptibody can range from about 1 nM to 1M.

In embodiments where an optional auxiliary active agent is included in the pharmaceutical formulation, the therapeutically effective amount of the auxiliary active agent will vary depending on the auxiliary active agent. In some embodiments, the therapeutically effective amount of the optional auxiliary active agent can range from 0.001 micrograms to about 1000 milligram. In other embodiments, the therapeutically effective amount of the optional auxiliary active agent can range from about 0.01 IU to about 1000 IU. In further embodiments, the therapeutically effective amount of the auxiliary active agent can range from 0.001 mL to about 1 mL. In yet other embodiments, the therapeutically effective amount of the optional auxiliary active agent can range from about 1% w/w to about 50% w/w of the total pharmaceutical formulation. In additional embodiments, the therapeutically effective amount of the optional auxiliary active agent ranges from about 1% v/v to about 50% v/v of the total pharmaceutical formulation. In still other embodiments, the therapeutically effective amount of the optional auxiliary active agent ranges from about 1% w/v to about 50% w/v of the total pharmaceutical formulation.

Dosage Forms

In some embodiments, the pharmaceutical formulations described herein can be in a dosage form. The dosage forms can be adapted for administration by any appropriate route. Appropriate routes include, but are not limited to, oral (including buccal or sublingual), rectal, epidural, intracranial, intraocular, inhaled, intranasal, topical (including buccal, sublingual, or transdermal), vaginal, intraurethral, parenteral, intracranial, subcutaneous, intramuscular, intravenous, intraperitoneal, intradermal, intraosseous, intracardiac, intraarticular, intracavernous, intrathecal, intravireal, intracerebral, and intracerebroventricular and intradermal. Such formulations can be prepared by any method known in the art.

Dosage forms adapted for oral administration can be discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as foam, spray, or liquid solution. In some embodiments, the oral dosage form can contain about 10 mg to 10 g of a pharmaceutical formulation containing an effective amount or an appropriate fraction thereof of the TertiapinQ peptibody. The oral dosage form can be administered to a subject in need thereof by a suitable administration method.

Where appropriate, the dosage forms described herein can be microencapsulated. The dosage form can also be prepared to prolong or sustain the release of any ingredient. In some embodiments, the TertiapinQ peptibody can be the ingredient whose release is delayed. In other embodiments, the release of an optionally included auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, PA: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings may be formed with a different ratio of water soluble polymer, water insoluble polymers, and/or pH dependent polymers, with or without water insoluble/water soluble non polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, the TertiapinQ peptibody, optional auxiliary active ingredient, and/or pharmaceutically acceptable salt thereof can be formulated with a paraffinic or water-miscible ointment base. In other embodiments, the active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, the TertiapinQ peptibody, the composition containing a TertiapinQ peptibody, auxiliary active ingredient, and/or pharmaceutically acceptable salt thereof in a dosage form adapted for inhalation is in a particle-size-reduced form that is obtained or obtainable by micronization. In some embodiments, the particle size of the size reduced (e.g. micronized) compound or salt or solvate thereof, is defined by a D50 value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active ingredient, which may be generated by various types of metered dose pressurized aerosols, nebulizers, or insufflators.

In some embodiments, the dosage forms are aerosol formulations suitable for administration by inhalation. In some of these embodiments, the aerosol formulation contains a solution or fine suspension of the TertiapinQ peptibody and/or pharmaceutically acceptable salt thereof, and a pharmaceutically acceptable aqueous or non-aqueous solvent. Aerosol formulations can be presented in single or multi-dose quantities in sterile form in a sealed container. For some of these embodiments, the sealed container is a single dose or multi-dose nasal or an aerosol dispenser fitted with a metering valve (e.g. metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of a TertiapinQ peptibody or a pharmaceutical formulation thereof. In further embodiments, the aerosol formulation also contains co-solvents and/or modifiers incorporated to improve, for example, the stability and/or taste and/or fine particle mass characteristics (amount and/or profile) of the formulation. Administration of the aerosol formulation can be once daily or several times daily, for example 2, 3, 4, or 8 times daily, in which 1, 2, or 3 doses or more are delivered each time.

For some dosage forms suitable and/or adapted for inhaled administration, the pharmaceutical formulation is a dry powder inhalable formulation. In addition to the TertiapinQ peptibody, an optional auxiliary active ingredient, and/or pharmaceutically acceptable salt thereof, such a dosage form can contain a powder base such as lactose, glucose, trehalose, manitol, and/or starch. In some of these embodiments, the TertiapinQ peptibody, optional auxiliary active ingredient, and/or pharmaceutically acceptable salt thereof is in a particle-size reduced form. In further embodiments, a performance modifier, such as L-leucine or another amino acid, cellobiose octaacetate, and/or metals salts of stearic acid, such as magnesium or calcium stearate.

In some embodiments, the aerosol formulations are arranged so that each metered dose of aerosol contains a predetermined amount of an active ingredient, such as the one or more of the TertiapinQ peptibodies described herein.

Dosage forms adapted for vaginal administration can be presented as pessaries, tampons, creams, gels, pastes, foams, or spray formulations. Dosage forms adapted for rectal administration include suppositories or enemas.

Dosage forms adapted for parenteral administration and/or adapted for any type of injection (e.g. intravenous, intraocular, intraperitoneal, subcutaneous, intramuscular, intradermal, intraosseous, epidural, intracardiac, intraarticular, intracavernous, intrathecal, intravitreal, intracerebral, and intracerebroventricular) can include aqueous and/or non-aqueous sterile injection solutions, which can contain anti-oxidants, buffers, bacteriostats, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and resuspended in a sterile carrier to reconstitute the dose prior to administration. Extemporaneous injection solutions and suspensions can be prepared in some embodiments, from sterile powders, granules, and tablets.

Dosage forms adapted for ocular administration can include aqueous and/or non-aqueous sterile solutions that can optionally be adapted for injection, and which can optionally contain anti-oxidants, buffers, bacteriostats, solutes that render the composition isotonic with the eye or fluid contained therein or around the eye of the subject, and aqueous and non-aqueous sterile suspensions, which can include suspending agents and thickening agents.

For some embodiments, the dosage form contains a predetermined amount of the TertiapinQ peptibody per unit dose. In an embodiment, the predetermined amount of the TertiapinQ peptibody is an effective amount of the TertiapinQ peptibody. In other embodiments, the predetermined amount of the TertiapinQ peptibody can be an appropriate fraction of the effective amount of the active ingredient. Such unit doses may therefore be administered once or more than once a day. Such pharmaceutical formulations may be prepared by any of the methods well known in the art.

Methods of Using the TertiapinQ Peptibodies and Formulations Thereof

The TertiapinQ peptibodies and formulations thereof can be administered to a subject in need thereof. The subject in need thereof can have AF. The subject in need thereof can have chronic AF. The TertiapinQ peptibodies and formulations thereof provided herein can be capable of reducing and/or blocking $I_{KACh}$ in the subject in need thereof. The TertiapinQ peptibodies thereof provided herein can be capable of reducing and/or blocking $I_{KACh}$ while having minimal effects on the atrial action potential in a normal heart. The TertiapinQ peptibodies and formulations thereof provided herein can be capable of prolonging action potential duration in atrial myocytes in the subject in need thereof. The TertiapinQ peptibodies and formulations thereof provided herein can be capable of terminating cholinergic AF without effecting ventricular electrophysiology in the subject in need thereof. The TertiapinQ peptibodies and formulations thereof provided herein can have an increased half-life when administered in vivo as compared to a TertiapinQ peptide alone. The TertiapinQ peptibodies and formulations thereof can treat AF or a symptom thereof in a subject. In some embodiments, the AF is chronic AF. In some embodiments, the amount of the TertiapinQ peptibody or formulation thereof can be an effective amount.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Figure 2:
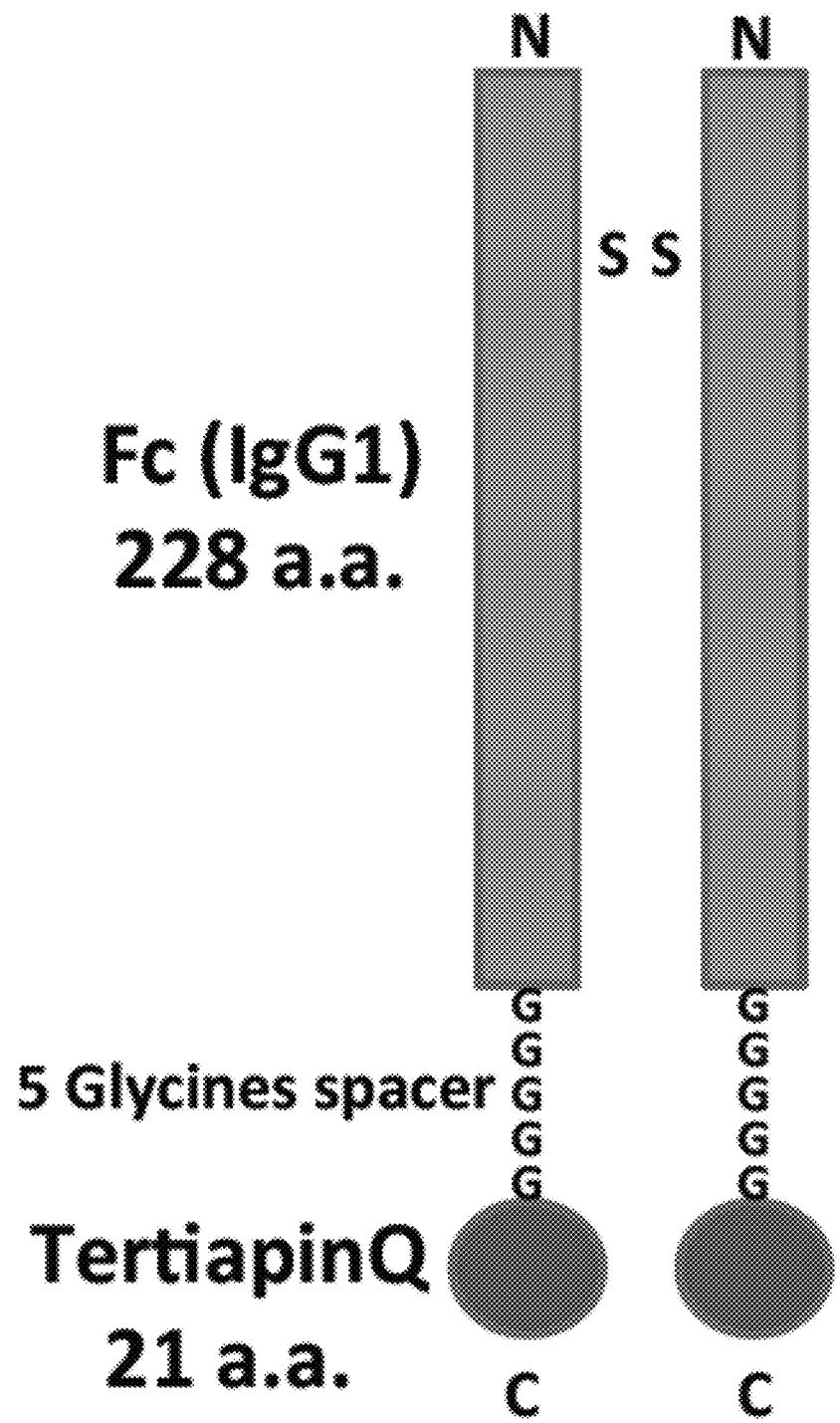
FIG. 2 is a cartoon of an engineered TertiapinQ peptibody.
Figure 3:
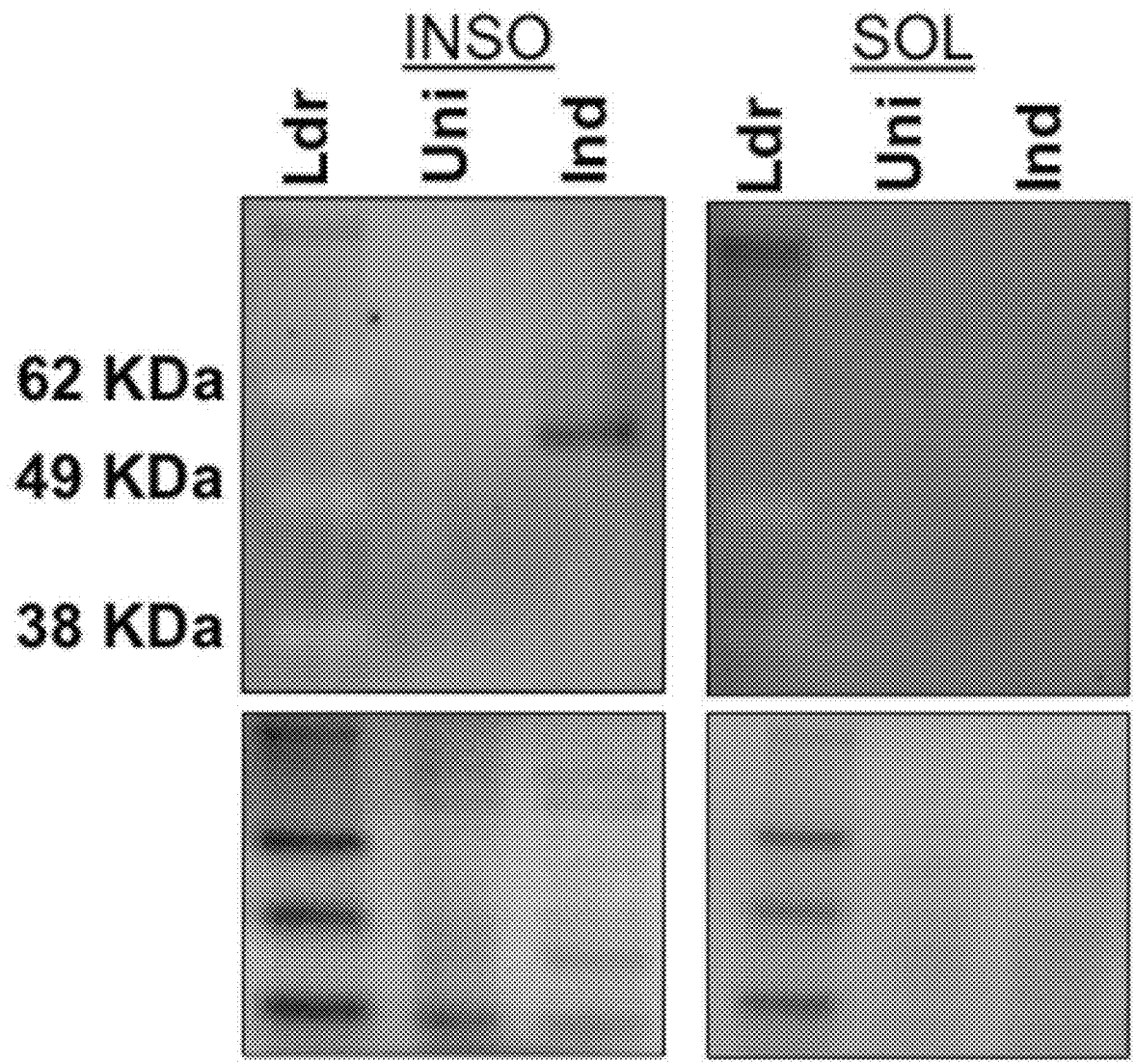
FIG. 3 shows the results from a Western blot (upper panels) and Ponceau stain (lower panels) of the insoluble fraction (INSO) and soluble fraction (SOL) to detect expression of a TertiapinQ peptibody. The 55 kDa peptibody was expressed in the inclusion body fraction (INSO) of the IPTG induced E. coli (ind) but not in the uninduced (uni) or in the soluble fraction (SOL). The left lane in each panel is the ladder marker (ldr).

FIG. 2 is a cartoon of an engineered TertiapinQ peptibody. The TertiapinQ was incorporated at the C-terminus of the Fc region at the N-terminus of TertiapinQ as the C-terminus of TertiapinQ has been observed to be involved in binding to its protein target. A 5 glycine linker between the Fc fragment and N-terminus of TertiapinQ has been introduced in order to decrease the rigidity of the fusion molecule, and allow for flexibility in ligand binding. The DNA sequence of the peptibody was codon optimized for protein expression in E. coli, de novo synthesized, and then cloned into the pET-Ub system. BL21DE3 E. coli were transformed with the construct and protein expression was induced with IPTG in a 20 ml miniculture. As a control, a similar miniculture was not induced with IPTG. After cell lysis, the soluble fraction was extracted in a buffer containing 25 mM Tris, 100 mM NaCl, pH=8, and solubilized the inclusion bodies in high SDS containing buffer. Protein samples of the soluble and insoluble fractions from the IPTG induced and uninduced bacteria were separated by electrophoresis, transferred on a PVDF membrane, and finally probed with Ponceau red staining and with PE-conjugated mouse anti-human IgG antibody (Jackson Immune). FIG. 3 shows that the peptibody at about 55 kDa, which was very close to the predicted molecular weight of the disulfide bond joined dimer (FIG. 2) was present in the insoluble fraction similarly to Romiplostim, a peptibody that is approved for clinical use.

Figures 4A, 4B, 4C, 4D, 4E, 4F:
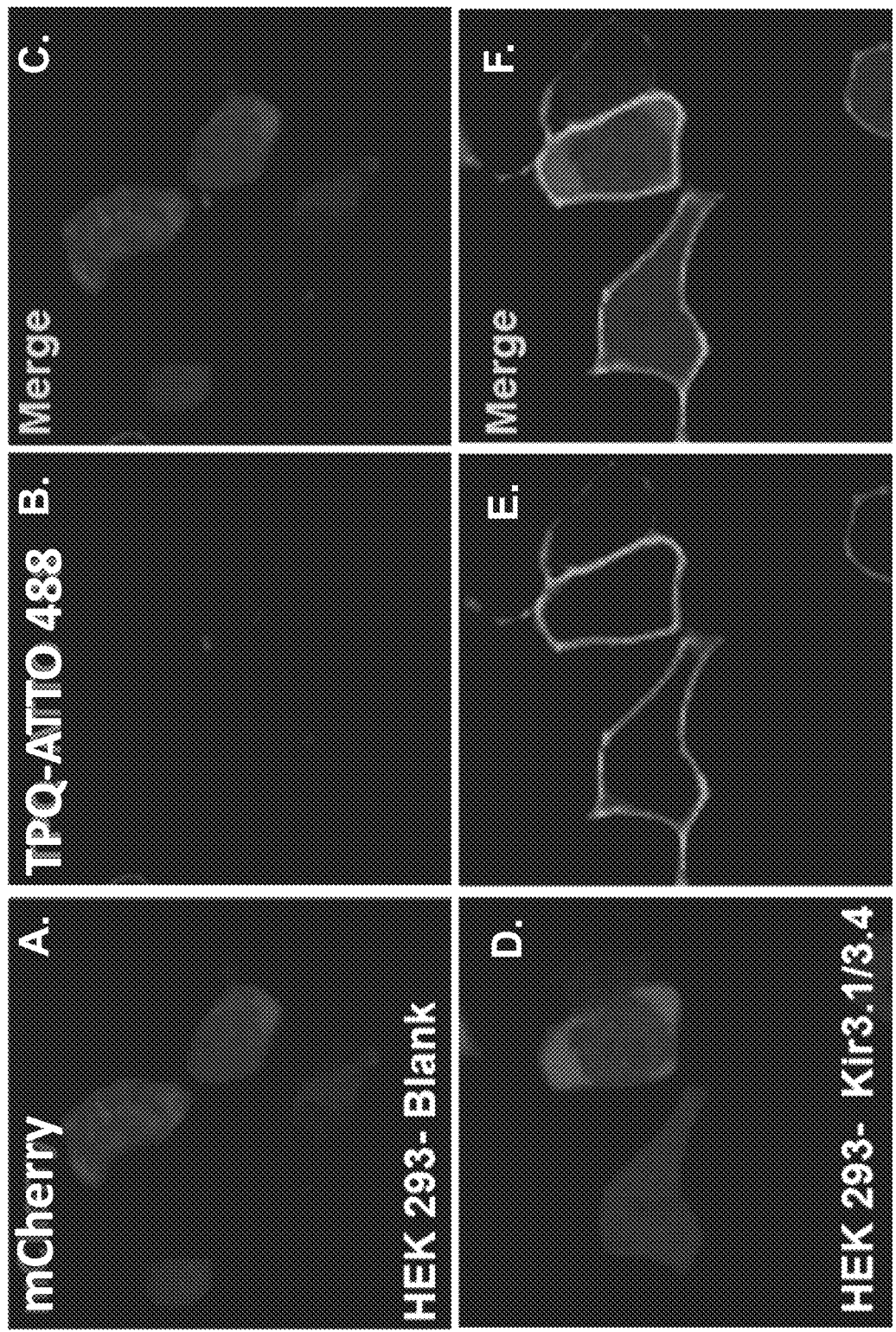
FIGS. 4A-4F show fluorescent confocal microscopic images that can demonstrate the ability of TertiapinQ labeled with ATT0488, which fluoresces in the 488 nm range (Alomone labs), to bind to Kir3.1/Kir3.4.

FIGS. 4A-4F demonstrates the ability of TertiapinQ labeled with ATT0488, which fluoresces in the 488 nm range (Alomone labs), to bind to Kir3.1/Kir3.4. FIGS. 4A-4C show fluorescent confocal microscopy images of live, blank, unpermeabilized HEK cells and incubated for 30 seconds with 50 nM TertiapinQ-ATT0488. No binding of TertiapinQ-ATT0488 was observed in the green channel. FIGS. 4D-4F can demonstrate clear membrane labeling of Kir3.1/Kir3.4 in unpermeabilized HEK293 cells stably expressing the proteins. Laser and detector settings were identical for all FIGS. 4A-4F.

Figure 5A:
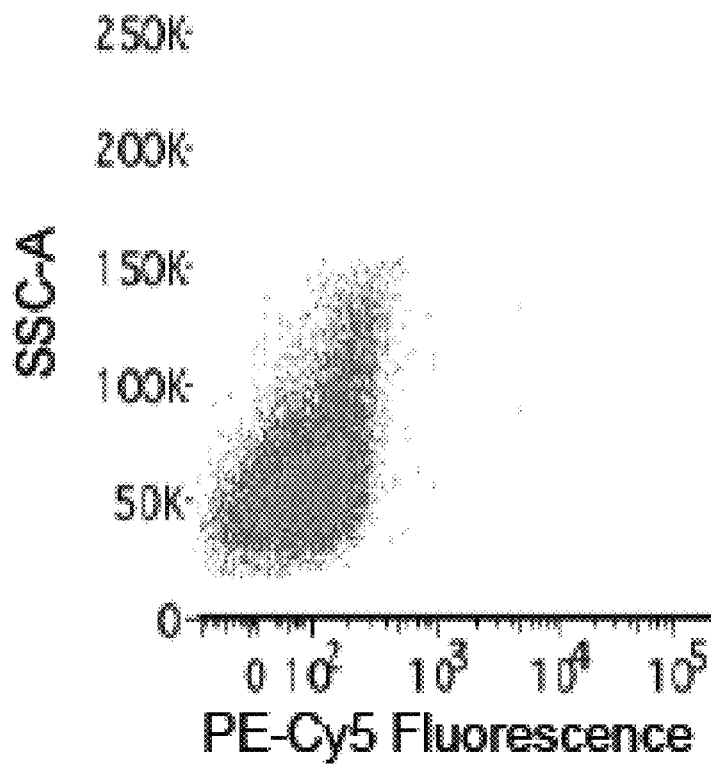
FIGS. 5A-5D show the results from a flow cytometry experiment in unpermeabilized HEK cells that were stably transfected with Kir3.1/3.4.
Figure 5B:
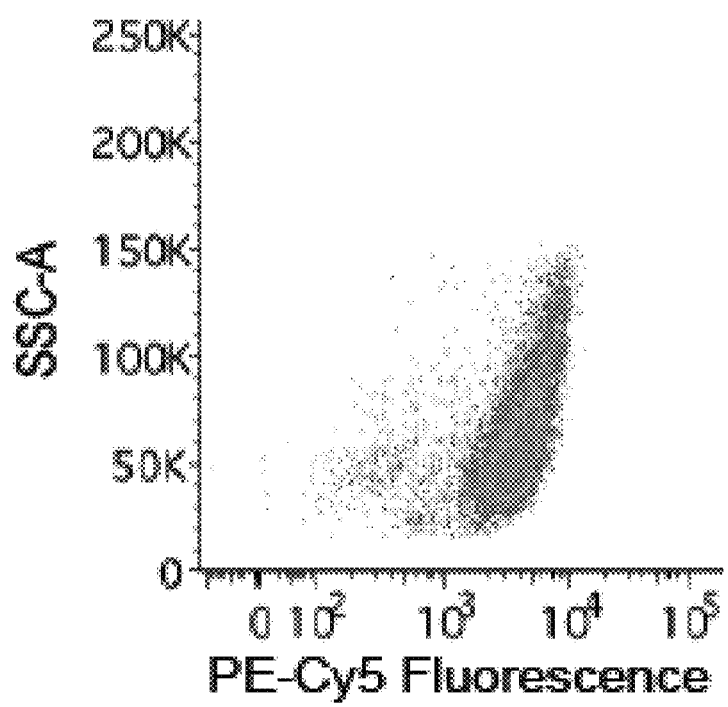
Figure 5C:
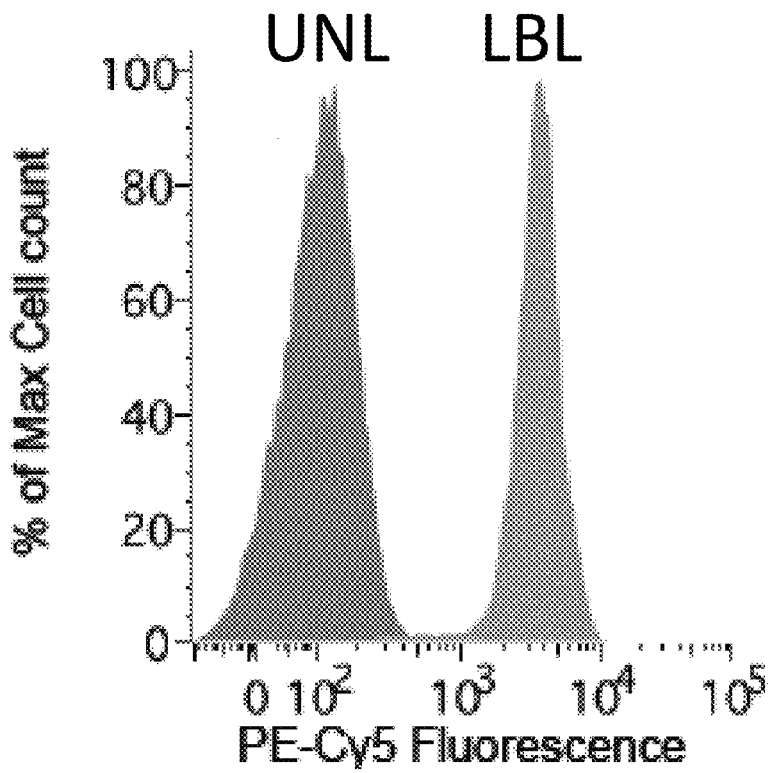
Figure 5D:
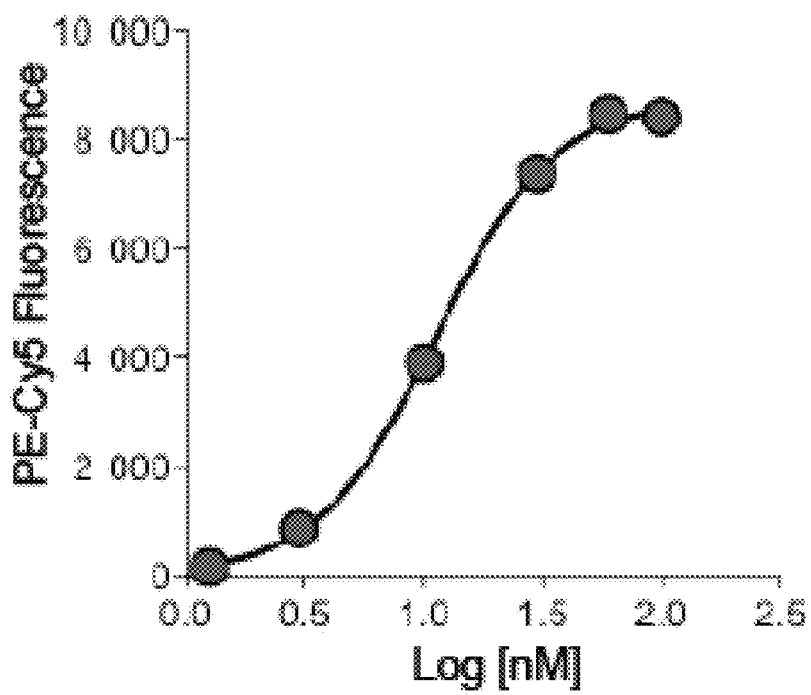

FIGS. 5A-5D show the results from a flow cytometry experiment in unpermeabilized HEK cells that were stably transfected with Kir3.1/3.4. These results demonstrate the robustness of TertiapinQ labeled with ATT0633 (Aiomone Labs) in the quantification of TertiapinQ binding to its target. FIG. 5A shows a plot of side scater versus PE-Cy5 fluorescence of a population of live, unlabeled HEK cells. In FIG. 5C, the gray curve is the histogram of the distribution of 50,000 events from FIG. 5A. The median fluorescence is 162 A.U. FIG. 5B is a plot of side scatter versus PE-Cy5 fluorescence of the HEK cells labeled with 10 nM TertiapinQ-ATT0688. A clear shift in the fluorescence of the live population was observed. In FIG. 5C, the right curve is the histogram of the distribution of 50,000 events from FIG. 5B. The median fluorescence is 3845 A.U. FIG. 5D shows a graph demonstrating a dose response curve of TertiapinQ-ATT0633 binding to Kir3.1/Kir3.4. The IC50 is 11 nM.

Figure 6B:
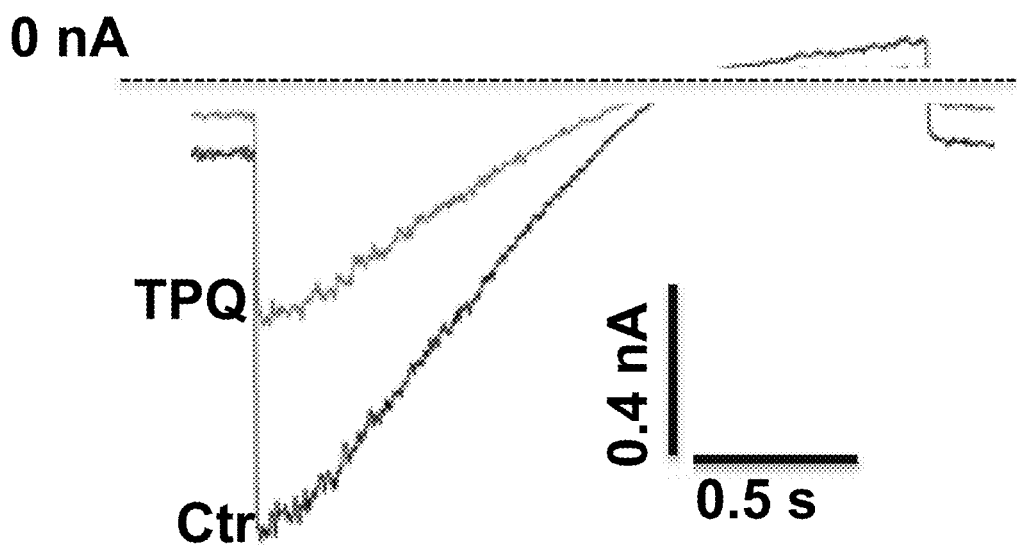
FIGS. 6A-6B shows the results from a patch clamp experiment in the Kir3.1/3.4 stably transfected HEK cells in response to a ramp in the absence (Ctr trace) and the presence (TPQ trace) of 50 nM TertiapinQ (FIG. 6A) and a dose response curve of $I_{KACh}$ block by TertiapinQ (FIG. 6B).
Figure 6A:
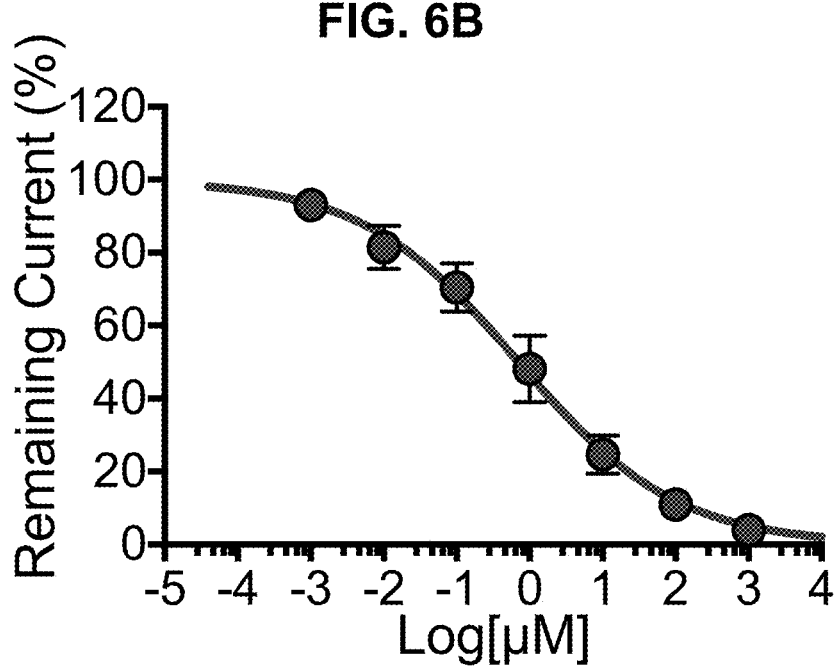

FIG. 6A shows the results from a patch clamp experiment in the Kir3.1/3.4 stably transfected HEK cells showing a basal, muscarinic stimulation independent, barium sensitive current, which decreased upon addition of 50 nM TertiapinQ. The recordings were performed in 50 mM extracellular K+, and a liquid junction potential of about −5 mV was not adjusted. The stably transfected HEK cells have a basal $I_{KACh}$ current due to the presence of background Gi protein signaling. FIG. 6B shows a dose response curve of TertiapinQ block of $I_{KACh}$ in the HEK cells. IC50=70 nM, Hill coefficient=1.2, $R^2$=0.99, n=5.

Figure 7:
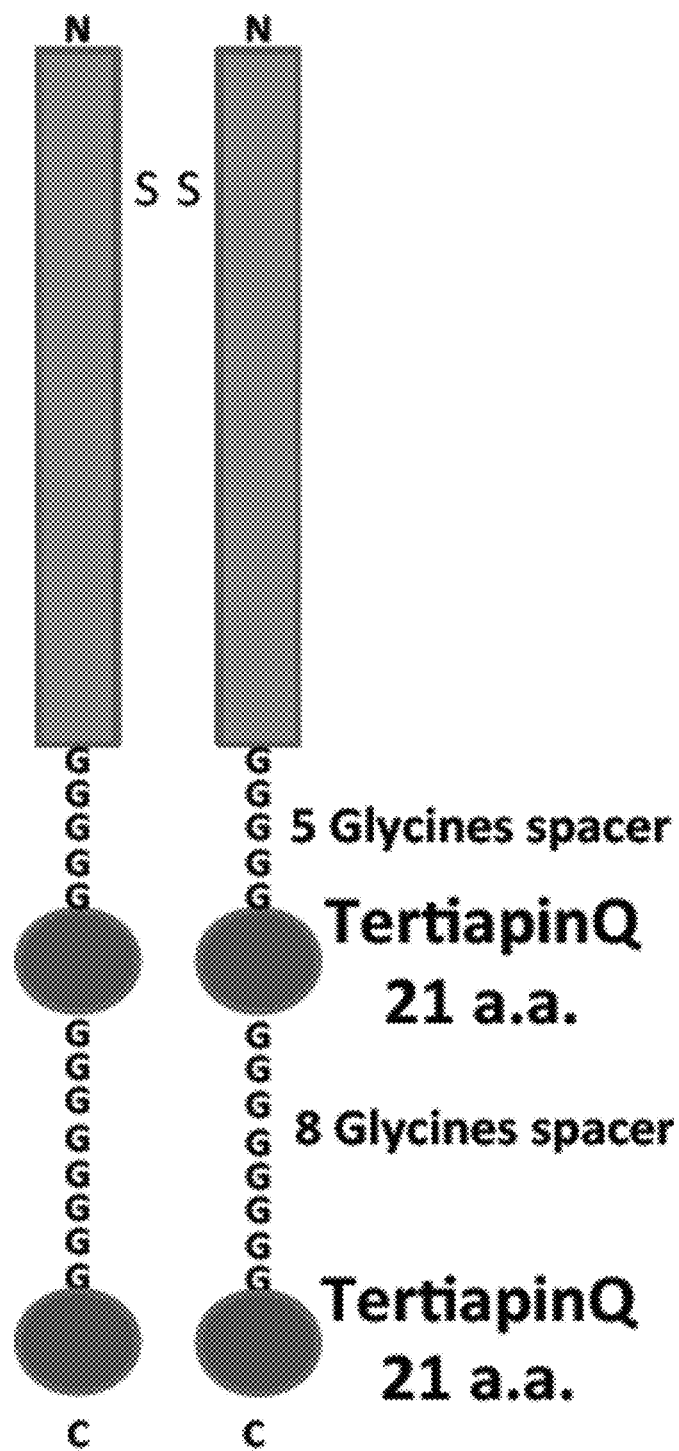
FIG. 7 shows a cartoon of a TertiapinQ peptibody having two copies of the TertiapinQ peptide linked via linkers to the Fc portion of the peptibody.

In view of this, a TertiapinQ peptibody has been designed as shown in FIG. 7 that contains two TertiapinQ peptides per Fc portions. The first TertiapinQ peptide will be linked at its N-terminus to the C-terminus of the Fc portion via a 5 glycine linker. The second TertiapinQ peptide will be linked at its N-terminus to the C-terminus of the first TertiapinQ peptide via an 8 glycine linker. This TertiapinQ peptibody DNA construct will be de novo synthesized similarly to the previously described and characterized TertiapinQ peptibody in this Example.

Example 2

Figures 8A, 8B, 8C, 8D, 8E, 8F, 8G, 8H, 8I:
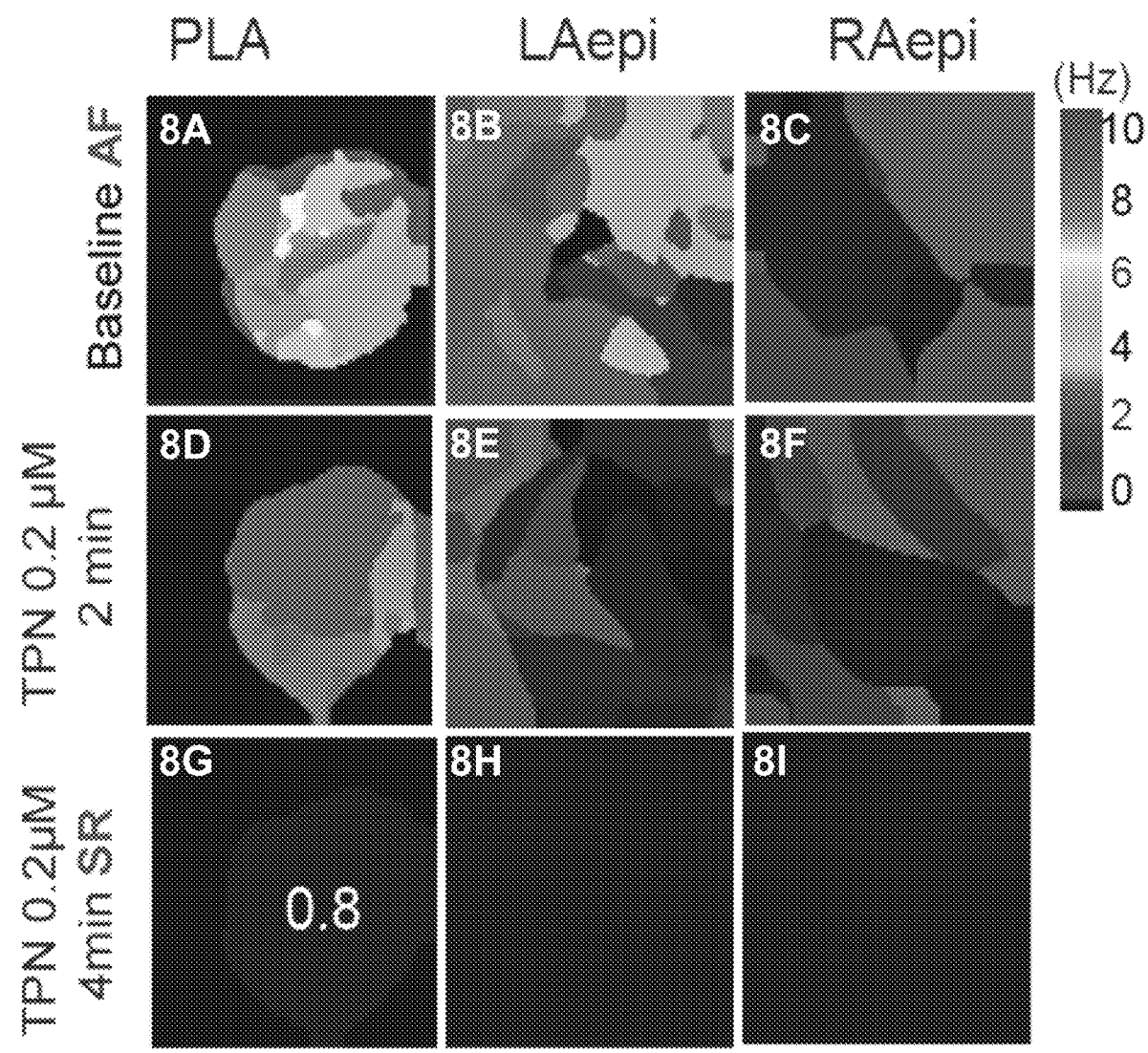
FIGS. 8A-8K shows the dominant frequency maps FIGS. 8A-8I) and graphs (FIGS. 8K and 8J) of the posterior left atrium (PLA), right atria (RA), and left atria (LA) at baseline, 2 minutes after 200 nM tertiapinQ, and right after AF termination.
Figure 8J:
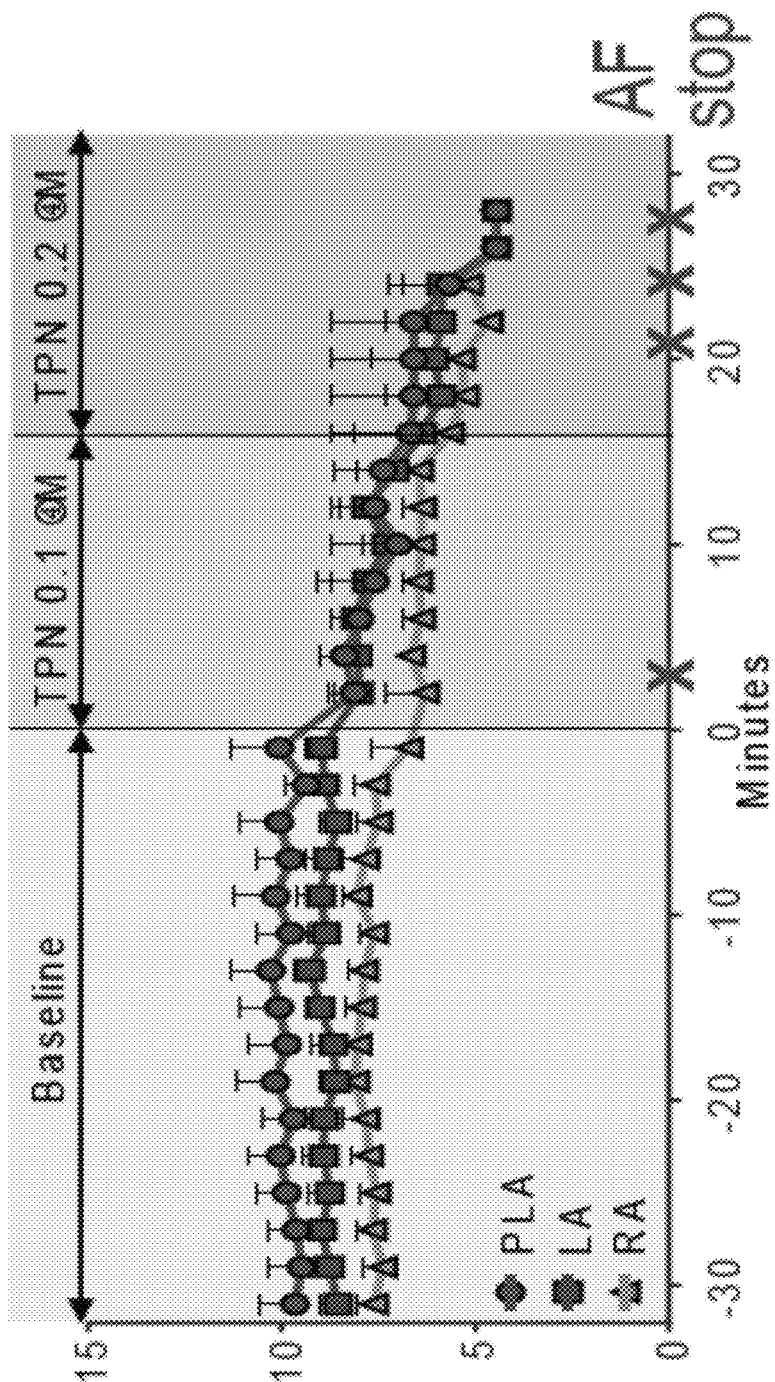
Figure 8K:
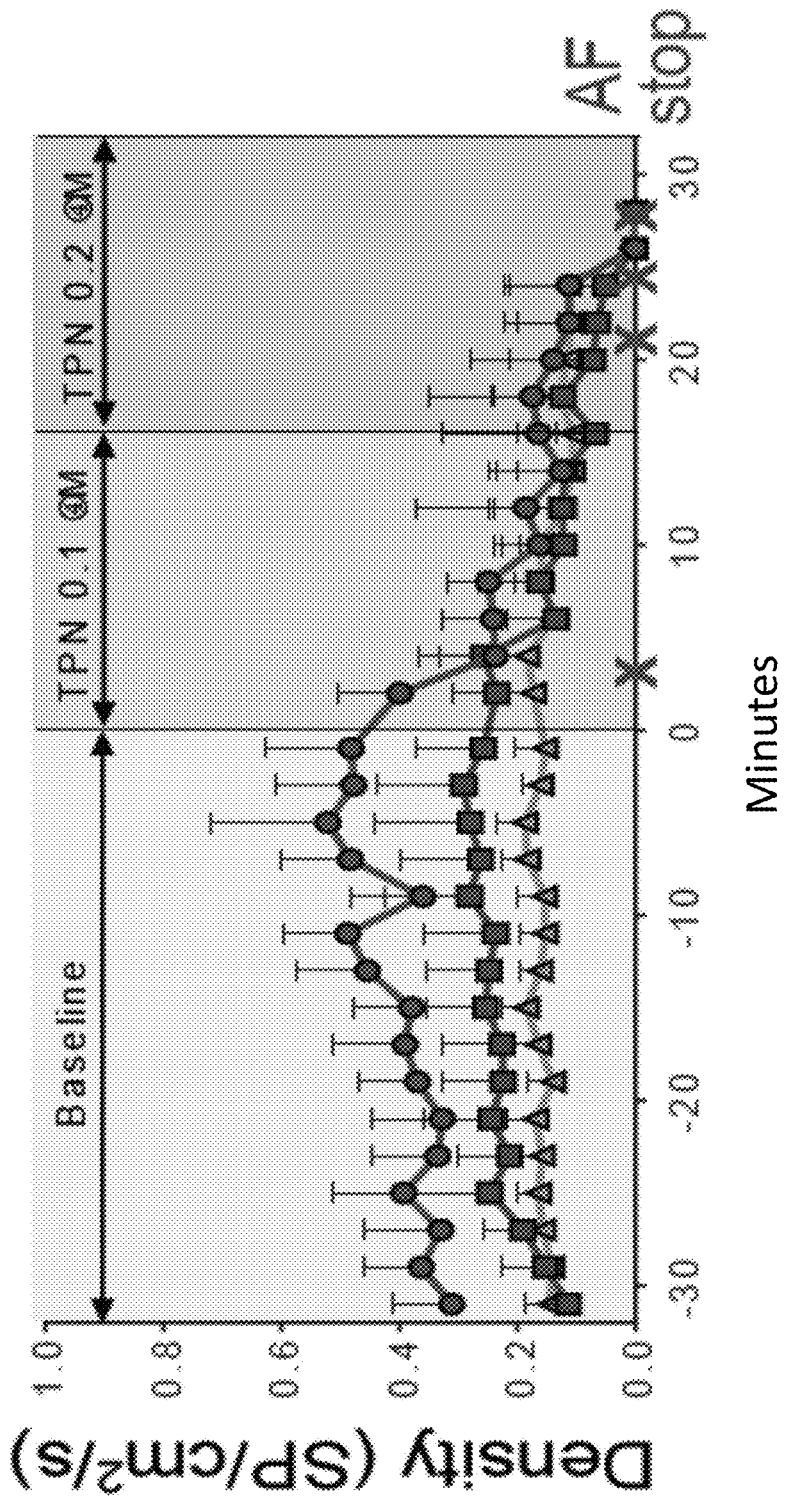

Constitutively active $I_{KACh}$ is a hallmark of remodeling in the chronically fibrillating atria. In Isolated Langendorff-perfused sheep hearts with tachypacing induced chronic/persistent atrial fibrillation, TertiapinQ (100 to 200 nM) was observed to restore sinus rhythm in 4 out of 5 hearts. FIGS. 8A-8I shows an example of dominant frequency maps of the posterior left atrium (PLA), left and right atria (LA, RA), at baseline, and after application of 200 nM TertiapinQ in a heart. TertiapinQ was observed to decrease the dominant frequency (DF) in the 3 regions 2 minutes after application, and after 4 minutes of TertiapinQ, the heart reverted to normal sinus rhythm. FIGS. 8J and 8K show a time course of the average DF and singularity point (SP) density changes in 4 hearts. The X's along the X axis denote moment of AF termination. SP density and DF were measured with optical mapping every 2 minutes, for 30 minutes, before application of TertiapinQ, and also every 2 minutes after application of TertiapinQ.

Figures 9A, 9B:
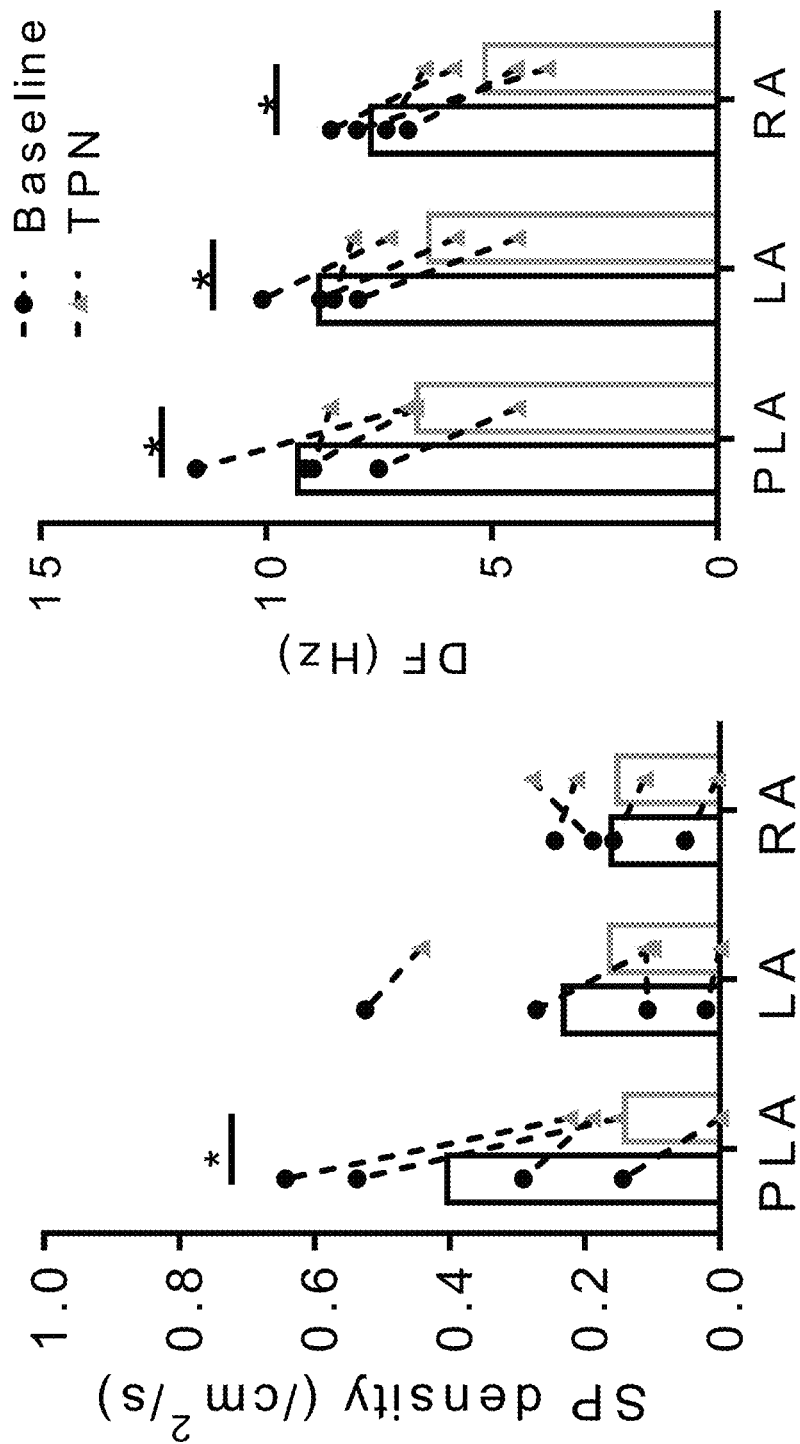
FIGS. 9A-9B show graphs demonstrating the quantifications of SP density (FIG. 9A) and DF (FIG. 9B) in the 4 hearts at baseline (black bars), and right before termination (grey bars).

FIGS. 9A-9B show graphs demonstrating the quantifications of SP density (FIG. 9A) and DF (FIG. 9B) in the 4 hearts at baseline, and right before termination. TertiapinQ significantly decreased SP density in the PLA, and significantly decreased DF in the PLA, LA, and RA. FIGS. 10A-10B show graphs demonstrating that $APD_{75}$ and $APD_{50}$ during pacing at 2.5 HZ are significantly prolonged in the PLA, LA, and RA by TertiapinQ. Action potentials at baseline were measured at the beginning of the experiment after the hearts were cardioverted with a DC shock. Subsequently, AF was re-induced with burst pacing. After termination of AF by TertiapinQ, the action potential duration was remeasured. It has been shown that Tertiapin has minimal effects on the action potential duration in normal atria.

Figure 11B:
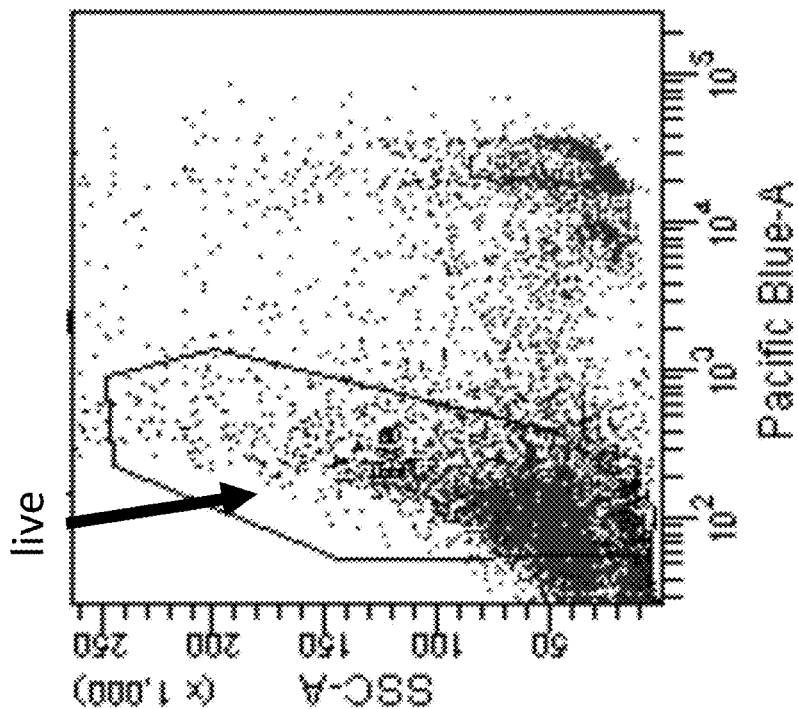
Figure 11A:
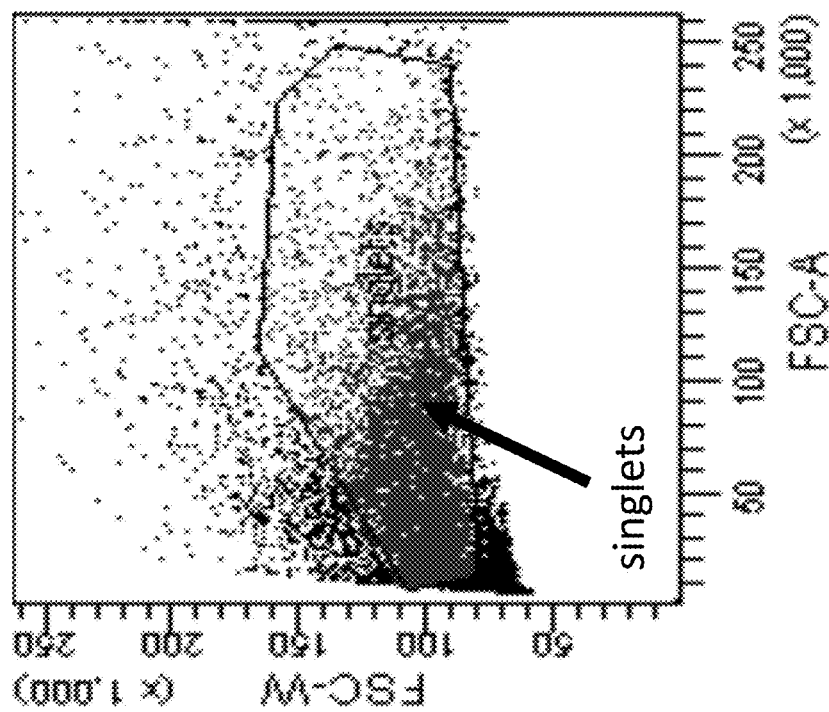
Figure 11F:
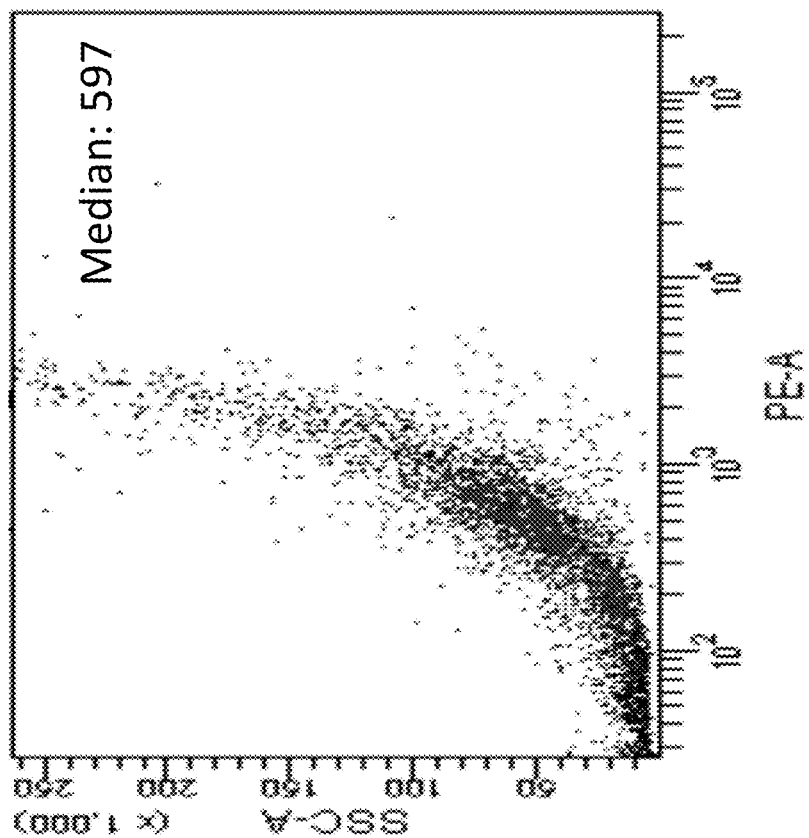
Figure 11E:
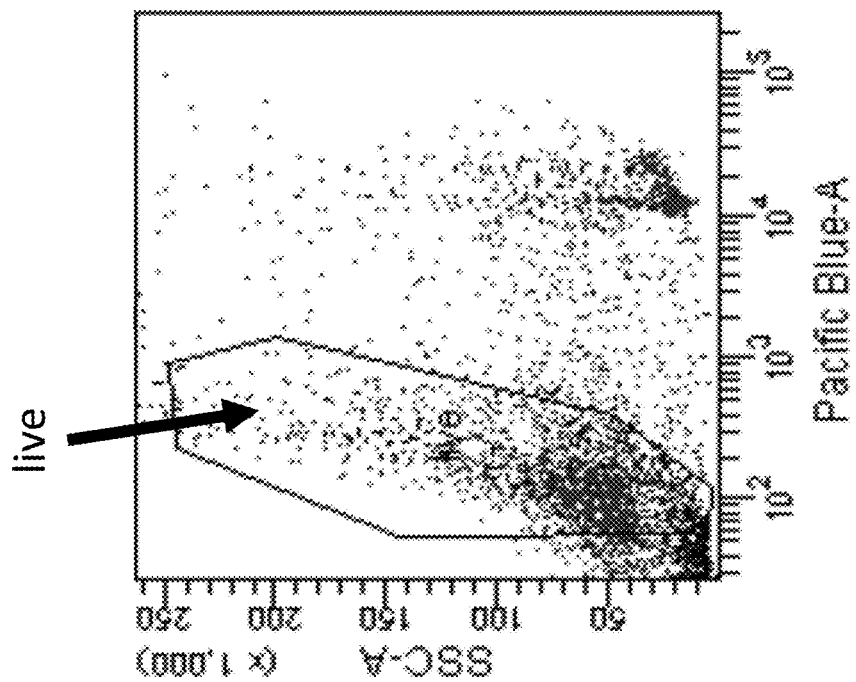
Figure 11H:
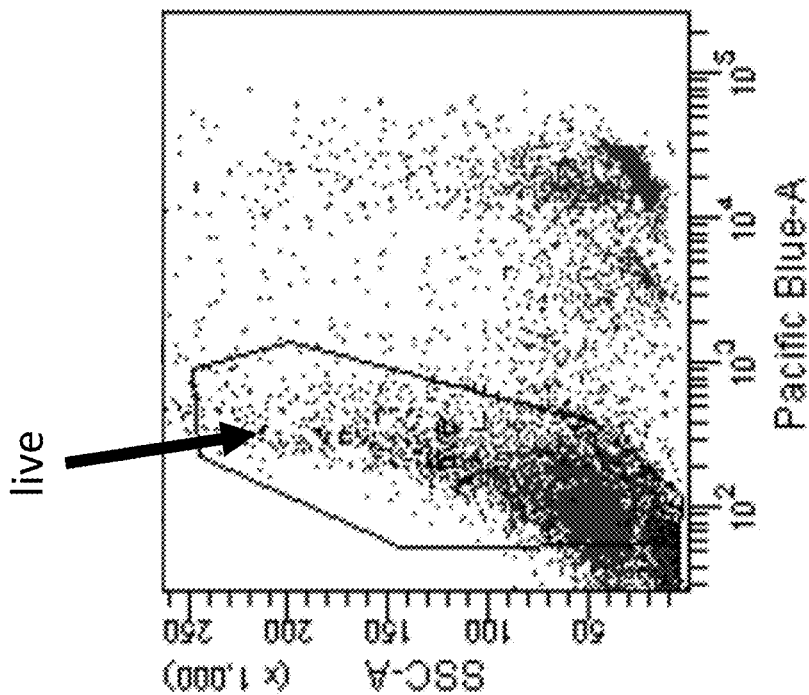
Figure 11G:
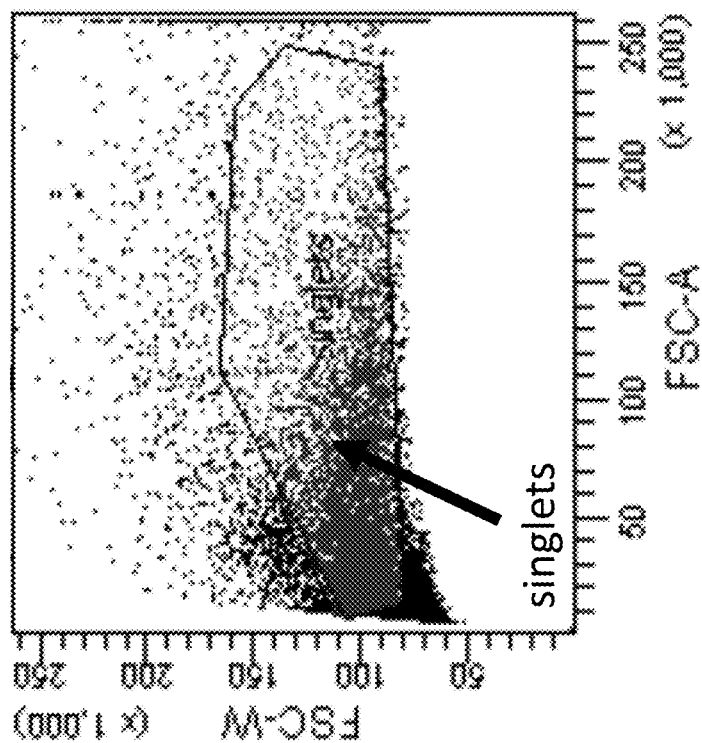
Figure 11I:
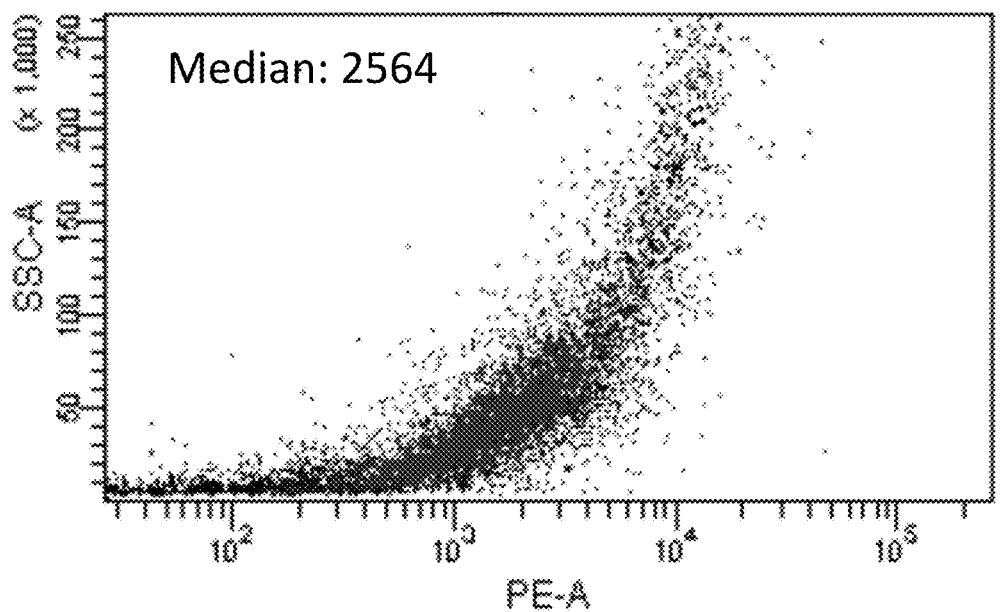

Live cell flow cytometry was also completed. Briefly, HEK293 cells were gently lifted with Acutase solution from the culture dish, dispersed, resuspended in phosphate buffered saline, and incubated for 30 minutes on ice with nothing, or PE conjugated secondary antibody only, or PE conjugated secondary antibody in addition to 0.01 µM peptibody. Flow cytometry was then carried out using a 4 laser/17 color BD LSR II machine. FIGS. 11A-11I show graphs of flow cytometry results that can demonstrate (FIGS. 11A-11C) negative control HEK293 cell stably expressing Kir3.1/3.4 (GIRK cells); (FIGS. 11D-11F) PE conjugated secondary antibody only; and (FIGS. 11G-11I) peptibody (about 0.01 µM) plus 2°-PE. FIGS. 11A, 11D, and 11G can demonstrate a gating strategy to select for single cells. FIGS. 11B, 11E, and 11H can show that the absence of DAPI staining was used to select live cells. FIGS. 11C, 11F, and 11I can show PE-fluorescence of a population of live, single cells.

Figure 12A:
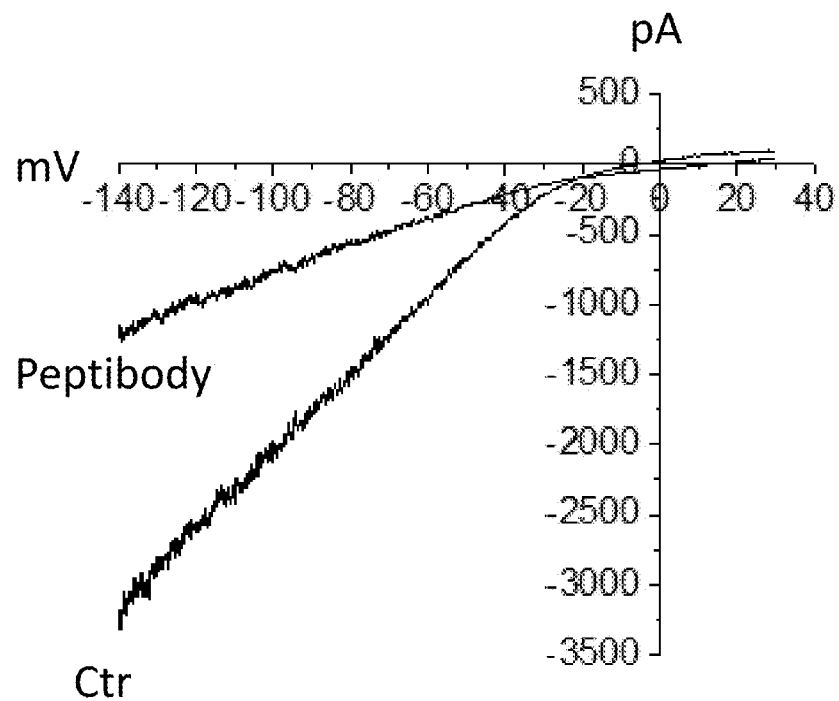
FIGS. 12A-12B show graphs that can demonstrate (FIG. 12A) $I_{KACh}$ recorded in GIRK cells in response to a ramp in the presence of about 0.1 µM Peptibody and (FIG. 12B) a dose response curve of $I_{KACh}$ block by TertiapinQ. $IC_{50}$=70 nM, $R^2$=0.95, n=5 and Peptibody, IC50=16 nM, $R^2$=0.9, n=5.
Figure 12B:
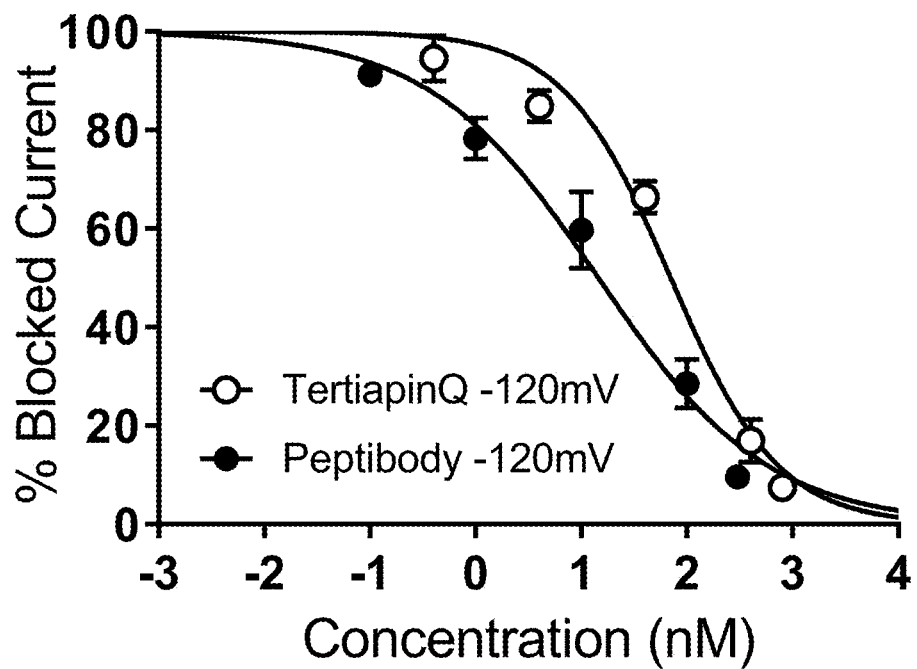

FIGS. 12A-12B show graphs that can demonstrate (FIG. 12A) $I_{KACh}$ recorded in GIRK cells in response to a ramp in the presence of about 0.1 µM Peptibody and (FIG. 12B) a dose response curve of $I_{KACh}$ block by TertiapinQ. IC50=70 nM, $R^2$=0.95, n=5 and Peptibody, IC50=16 nM, $R^2$=0.9, n=5.

We claim:

1. A peptibody comprising:
   a first monomer and a second monomer, wherein each monomer consists essentially of:
   an Fc polypeptide;
   a TertiapinQ peptide, wherein the N-terminus of the TertiapinQ peptide is linked to the C-terminus of the Fc polypeptide via a linker; and
   wherein the first monomer and the second monomer are attached via a disulfide bridge between the Fc polypeptide of the first monomer and the Fc polypeptide of the second monomer.

2. The peptibody of claim 1, wherein the Fc polypeptide is a human Fc polypeptide.

3. The peptibody of claim 1, wherein the Fc polypeptide has an amino acid sequence that is about 90% to 100% identical to SEQ ID NO.: 3 or 9.

4. The peptibody of claim 1, wherein the TertiapinQ peptide has an amino acid sequence that is about 85% to 100% identical to SEQ ID NO.: 4.

5. The peptibody of claim 1, wherein the first linker is a glycine linker.

6. The peptibody of claim 1, wherein the first linker is a glycine linker consisting of 5 glycine residues.

7. The peptibody of claim 1, wherein the Fc polypeptide has an amino acid sequence comprising SEQ ID NO.: 3.

8. The peptibody of claim 1, wherein the Fc polypeptide has an amino acid sequence comprising SEQ ID NO.: 9.

9. The peptibody of claim 1, wherein the TertiapinQ peptide has an amino acid sequence comprising SEQ ID NO.: 4.

10. The peptibody of claim 1, wherein the linker is a glycine linker consisting of 8 glycine residues.

11. A pharmaceutical formulation comprising:
an amount of a peptibody, wherein the peptibody comprises
a first monomer and a second monomer, wherein each monomer consists essentially of:
an Fc polypeptide;
a TertiapinQ peptide, wherein the N-terminus of the TertiapinQ peptide is linked to the C-terminus of the Fc polypeptide via a linker; and
wherein the first monomer and the second monomer are attached via a disulfide bridge between the Fc polypeptide of the first monomer and the Fc polypeptide of the second monomer; and
a pharmaceutically acceptable carrier.

12. The pharmaceutical formulation of claim 11, wherein the amount is an amount effective to block IKAch current in an atrial myocyte.

13. The pharmaceutical formulation as in claim 11, wherein the amount is an amount effective to treat chronic atrial fibrillation or a symptom thereof in a subject in need thereof.

14. The pharmaceutical formulation as in claim 11, wherein the Fc polypeptide has an amino acid sequence that is about 90% to 100% identical to SEQ ID NO.: 3 or 9.

15. The pharmaceutical formulation as in claim 11, wherein the TertiapinQ peptide has an amino acid sequence that is about 85% to 100% identical to SEQ ID NO.: 4.

16. A method of treating chronic atrial fibrillation in a subject in need thereof, the method comprising:
administering an amount of a peptibody or a pharmaceutical formulation thereof to a subject in need thereof, wherein the peptibody comprises
an amount of a peptibody, wherein the peptibody comprises
a first monomer and a second monomer, wherein each monomer consists essentially of:
an Fc polypeptide;
a TertiapinQ peptide, wherein the N-terminus of the TertiapinQ peptide is linked to the C-terminus of the Fc polypeptide via a linker; and
wherein the first monomer and the second monomer are attached via a disulfide bridge between the Fc polypeptide of the first monomer and the Fc polypeptide of the second monomer.

\* \* \* \* \*

SEQUENCE LISTING

```
<160> NUMBER OF SEQ ID NOS: 9

<210> SEQ ID NO 1
<211> LENGTH: 359
<212> TYPE: PRT
<213> ORGANISM: Artificial Sequence
<220> FEATURE:
<223> OTHER INFORMATION: TertiapinQ Peptibody having a single TertiapinQ
      peptide per monomer

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Gly Gly Gly Gly Gly Gly
            325                 330                 335

Gly Gly Ala Leu Cys Asn Cys Asn Arg Ile Ile Ile Pro His Gln Cys
            340                 345                 350

Trp Lys Lys Cys Gly Lys Lys
            355
```

<210> SEQ ID NO 2
<211> LENGTH: 385
<212> TYPE: PRT
<213> ORGANISM: Artificial Sequence
<220> FEATURE:
<223> OTHER INFORMATION: TertiapinQ Peptibody having two TertiapinQ
      peptides per monomer

<400> SEQUENCE: 2

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
```

```
                195                 200                 205
Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Gly Gly Gly Gly Gly Ala
                325                 330                 335

Leu Cys Asn Cys Asn Arg Ile Ile Ile Pro His Gln Cys Trp Lys Lys
                340                 345                 350

Cys Gly Lys Gly Gly Gly Gly Gly Gly Gly Ala Leu Cys Asn
            355                 360                 365

Cys Asn Arg Ile Ile Ile Pro His Gln Cys Trp Lys Lys Cys Gly Lys
370                 375                 380

Lys
385

<210> SEQ ID NO 3
<211> LENGTH: 330
<212> TYPE: PRT
<213> ORGANISM: Artificial Sequence
<220> FEATURE:
<223> OTHER INFORMATION: Human IgG1 Fc monomer

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
```

```
                    165                 170                 175
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 4
<211> LENGTH: 21
<212> TYPE: PRT
<213> ORGANISM: Artificial Sequence
<220> FEATURE:
<223> OTHER INFORMATION: TertiapinQ

<400> SEQUENCE: 4

Ala Leu Cys Asn Cys Asn Arg Ile Ile Ile Pro His Gln Cys Trp Lys
1               5                   10                  15

Lys Cys Gly Lys Lys
            20

<210> SEQ ID NO 5
<211> LENGTH: 1077
<212> TYPE: DNA
<213> ORGANISM: Artificial Sequence
<220> FEATURE:
<223> OTHER INFORMATION: cDNA sequence of a TertiapinQ peptibody with a
      single TertiapinQ peptide per monomer codon optimized for
      expression in E. coli.

<400> SEQUENCE: 5
gcaagtacaa aagggccttc ggttttccct ttggctccct ctagcaaatc cacatctggc      60
ggcacggccg ctttagggtg ccttgtgaag gattattttc agaaccagt gaccgtgtcc     120 tggaatagtg gagctcttac aagtggggtt catactttcc cagcagtgct gcaatctagc     180
gggttgtata gcctgagttc ggttgtgact gtgccatctt cttctttggg gactcagacg     240
tacatctgta atgtcaacca taagccgtcg aacaccaagg tagacaagaa agttgaacct     300
aagtcatgcg ataaaacgca cacctgtccc ccttgtcccg ccccggaatt gttaggtggg     360
ccttcggtgt tcttattccc gcccaagccg aaagatacgt tgatgatttc acgcacacct     420
gaggtgacct gcgtagtagt tgatgtatct cacgaagatc cagaagttaa atttaactgg     480
tatgtggatg gagtagaagt gcataatgca aagacgaaac cgcgcgaaga acagtataac     540
tctacctacc gcgtggtatc ggtcttgacc gtgctgcatc aagattggct taatggcaag     600
```

```
gagtataaat gcaaagtctc taataaagct ttacctgccc caattgaaaa aaccatctcg    660
aaggcaaagg gacagccacg tgagccgcaa gtgtacacat tacccccaag tcgtgatgaa    720
cttacgaaaa atcaagtatc tttgacgtgt ctggtaaagg ggttctatcc ttccgacatt    780
gcagtggagt gggagtctaa cggccaacca gagaacaact ataaaactac gcccccagtc    840
cttgatagcg atggatcgtt cttcttgtac tcgaagctga ctgtcgacaa gagtcgctgg    900
cagcaaggga atgtgttctc ctgttctgtt atgcacgaag cgttacataa ccattatact    960
cagaagtcac ttagtcttag ccctggtaaa gggggaggag gaggcggtgg tggtgccttg   1020
tgcaattgca accgtattat cattcctcat caatgctgga agaaatgtgg caaaaaa      1077
```

<210> SEQ ID NO 6
<211> LENGTH: 1077
<212> TYPE: DNA
<213> ORGANISM: Artificial Sequence
<220> FEATURE:
<223> OTHER INFORMATION: cDNA sequence of a TertiapinQ peptibody with a single TertiapinQ peptide per monomer codon optimized for expression in human cells.

<400> SEQUENCE: 6

```
gcatctacaa agggtccatc agtatttcca ctggcgccct catctaagtc aacgagtgga     60
ggaacggctg cgctgggatg cctcgtaaaa gattacttcc cagagccagt tacggtgagt    120
tggaactccg gagcccttac ttcaggagta cacacctttc cagcagttct ccaatcctcc    180
gggctctatt ccttgagttc tgtcgttacc gttccatcaa gttcactcgg gacgcaaacc    240
tatatttgca acgttaatca caaaccctct aacacgaaag tagacaagaa ggtagaaccc    300
aagtcctgcg acaagacaca cacttgccct ccgtgcccgg cgcctgagct ccttggtggt    360
ccatcagtgt ttcttttttcc cccgaaacct aaggatacat tgatgatttc ccgcactccc    420
gaggttactt gtgttgtagt ggatgtctcc catgaggacc cagaagtaaa gttcaactgg    480
tacgttgacg gggtggaggt acacaacgcg aaaactaagc cacgggaaga gcagtacaat    540
tcaacataca gggttgtgtc tgttcttacg gttctgcacc aggattggtt gaatgggaag    600
gagtataagt gtaaggtcag taataaggca ttgccagcgc aatagaaaaa gacgatcagc    660
aaagccaagg gacagccaag ggagccacaa gtctacactc ttccgcccag tcgcgatgag    720
ctgacgaaga accaggtatc cttgacctgt ttggtaaaag ggtttttatcc ctccgacata    780 gccgtagaat gggagtctaa cggtcaaccg gagaataatt acaaaactac tcccccggtg    840
ctcgatagtg atggttcttt ttttctgtat agtaaactga cggtggacaa gtcaagatgg    900
caacagggta acgtattcag ttgtagtgtc atgcacgagg ctctccataa tcactatacg    960
caaaagagtc tgagcctctc tccgggtaag ggggtggtg gtggaggcgg gggtgcgctt   1020
tgtaattgta atcggataat cataccacat caatgttgga agaagtgtgg aaaaaag     1077
```

<210> SEQ ID NO 7
<211> LENGTH: 1155
<212> TYPE: DNA
<213> ORGANISM: Artificial Sequence
<220> FEATURE:
<223> OTHER INFORMATION: cDNA sequence of a TertiapinQ peptibody with two TertiapinQ peptides per monomer per monomer codon optimized for expression in E. coli.

<400> SEQUENCE: 7

```
gccagtacca aaggtccgag cgtattccca ttggcccccat cctctaaatc gacgtcgggc     60
```

| | |
|---|---:|
| ggaacggcgg cccttggctg tctggtcaaa gactatttc ctgaacccgt aacggtgtcc | 120 |
| tggaactcgg gggcattaac ctccggagta cacacttttc ccgctgtgtt acaatcatcg | 180 |
| ggtctttatt ctcttagttc cgtggtaaca gttccatcat catccttagg cacccaaacg | 240 |
| tacatctgca atgtcaacca caagccatcc aacaccaaag tagacaaaaa ggttgaaccg | 300 |
| aaatcctgtg acaaaacaca tacatgtcct ccgtgccccg ctccggagtt gctgggcgga | 360 |
| ccatcagtct tttatttcc accaaagcca aggacacct tgatgatctc ccgtactcca | 420 |
| gaggtaactt gcgtagtggt ggatgtcagc cacgaggatc ctgaagtaaa attcaattgg | 480 |
| tatgtagatg gtgtagaagt gcataatgcg aagacaaagc cacgtgagga gcagtataac | 540 |
| agcacttacc gtgtagtatc agtcttaacc gtcctgcatc aggattggct taacggtaag | 600 |
| gaatacaaat gcaaagtaag caataaagca ctgcccgctc ctatcgagaa acgatctcc | 660 |
| aaagcaaagg ggcaaccacg tgaacctcag gtgtacacct gccgccttc gcgcgatgag | 720 |
| cttactaaaa atcaggtatc gttgacgtgt ctggttaaag gtttctaccc ctcagacatc | 780 |
| gctgtagaat gggagtcgaa tggccagcca gaaaacaact acaaaacgac gcctcccgtc | 840 |
| ttagattctg acggctcttt tttcctgtac tcaaagttga cggtggacaa gtcccgctgg | 900 |
| cagcagggca atgtgttctc gtgttcggtg atgcacgagg ccttgcacaa ccattataca | 960 |
| caaaaaagcc tttcattgtc cccaggaaaa gggggtggcg ggggagccct gtgtaattgc | 1020 |
| aaccgtatta tcattccaca tcagtgttgg aagaaatgcg gtaagaaggg gggtggtggt | 1080 |
| ggaggaggcg gggccctttg taattgtaac cgtattatta tcccacatca atgctggaag | 1140 |
| aagtgtggga aaaa | 1155 |

<210> SEQ ID NO 8
<211> LENGTH: 1155
<212> TYPE: DNA
<213> ORGANISM: Artificial Sequence
<220> FEATURE:
<223> OTHER INFORMATION: cDNA sequence of a TertiapinQ peptibody with
      two TertiapinQ peptides per monomer per monomer codon optimized
      for expression in human.

<400> SEQUENCE: 8

| | |
|---|---:|
| gcgagcacca agggccctag tgtcttccct ctcgcgccat catctaaaag tacaagtgga | 60 |
| gggactgccg ctctcggctg tcttgtcaag gattactttc ctgaacccgt cactgttccc | 120 |
| tggaactcag gcgctttgac gtctggtgtg catacctttc ccgcggtcct tcaatcaagt | 180 |
| ggactgtata gcctcagtag tgtcgtaacc gttccctcat caagtctcgg tacccaaacg | 240 |
| tacatttgca acgttaatca taaaccttct aacacaaaag tagataagaa ggttgaacca | 300 |
| aaatcttgtg ataagacaca tacctgcccct ccttgtcccg cgcctgaact gttggggggt | 360 |
| cctagcgtat tcctttttccc cccaaaaacca aggacactc tcatgataag tcggacgccc | 420 |
| gaggtcacttt gcgtggttgt cgacgtcagt cacgaagacc cggaggtcaa attcaattgg | 480 |
| tacgtagacg gggtggaggt gcataacgca aaaactaaac ctcgcgagga gcaatacaac | 540 |
| tcaacctacc gagtcgttag cgttctgacg gtgcttcatc aggattggct gaacggtaaa | 600 |
| gagtataaat gtaaagttag taataaggcc ctgccggcac ctattgagaa acaatctca | 660 |
| aaggctaaag gacagccccg agagccacag gtatacacgt tgccgccctc cagggatgaa | 720 |
| cttacaaaga accaagtgtc cctcacgtgt ttggttaaag cttttatccc ctctgacata | 780 |
| gcagttgagt gggagagtaa cggtcaacca gagaacaact ataaaactac gcctccagtc | 840 |
| ttggattctg acgggtcctt ctttctgtat agcaaactta ccgtggacaa gtctagatgg | 900 |

```
cagcagggga acgttttctc ctgctccgta atgcatgaag ccctgcacaa ccactacacg      960
caaaagagtc tttctctgtc ccctggaaaa ggaggaggag gtggcgctct gtgcaactgc     1020
aacagaatca tcatacctca ccaatgttgg aagaagtgcg gaaagaaagg aggggggtgga    1080 ggcggtggtg gtgctttgtg caactgtaat agaataatta tcccgcatca gtgttggaag    1140
aagtgcggaa agaag                                                      1155
```

<210> SEQ ID NO 9
<211> LENGTH: 227
<212> TYPE: PRT
<213> ORGANISM: Artificial Sequence
<220> FEATURE:
<223> OTHER INFORMATION: truncated IgG Fc-Beginning at D104 of SEQ ID
      NO: 1

<400> SEQUENCE: 9

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys
225
```